United States Patent
Sato et al.

(10) Patent No.: US 9,560,999 B2
(45) Date of Patent: Feb. 7, 2017

(54) GLUCOSE TOLERANCE ANALYZER, GLUCOSE TOLERANCE ANALYZING SYSTEM, AND STORAGE MEDIUM

(71) Applicant: Sysmex Corporation, Kobe-shi (JP)

(72) Inventors: Toshiyuki Sato, Kobe (JP); Seiki Okada, Kobe (JP); Takeyoshi Fujiwara, Kobe (JP); Mariko Yuno, Kobe (JP); Shigenobu Egawa, Fukuoka (JP)

(73) Assignee: SYSMEX CORPORATION, Kobe (JP)

( * ) Notice: Subject to any disclaimer, the term of this patent is extended or adjusted under 35 U.S.C. 154(b) by 903 days.

(21) Appl. No.: 13/652,756

(22) Filed: Oct. 16, 2012

(65) Prior Publication Data

US 2013/0096842 A1    Apr. 18, 2013

(30) Foreign Application Priority Data

Oct. 17, 2011    (JP) ................. 2011-227955

(51) Int. Cl.
     *G01N 33/48*      (2006.01)
     *G01N 31/00*      (2006.01)
     (Continued)

(52) U.S. Cl.
     CPC ....... *A61B 5/150259* (2013.01); *A61B 5/1455* (2013.01); *A61B 5/14532* (2013.01); *A61B 5/14546* (2013.01); *A61B 5/1513* (2013.01); *A61B 5/1519* (2013.01); *A61B 5/150022* (2013.01); *A61B 5/15113* (2013.01);
     (Continued)

(58) Field of Classification Search
     None
     See application file for complete search history.

(56) References Cited

U.S. PATENT DOCUMENTS 7,452,687 B2    11/2008    Yamakoshi et al.
2003/0208113 A1*    11/2003    Mault et al. ................. 600/316
(Continued)

FOREIGN PATENT DOCUMENTS

CN    101762629 A    6/2010
CN    102024096 A    4/2011
(Continued)

*Primary Examiner* — Larry D Riggs, II
(74) *Attorney, Agent, or Firm* — Brinks Gilson & Lione

(57) ABSTRACT

A glucose tolerance analyzer comprising: an accepting section configured to accept inputs of information regarding a type of food or drink ingested by a subject, information regarding an intake amount of the food or drink, and information regarding an amount of glucose in the subject after the ingestion of the food or drink; an output section configured to output an analysis result of glucose tolerance; and a controller configured to: calculate a reference value for analyzing glucose tolerance of the subject based on the accepted information regarding the type of the food or drink ingested by the subject and the information regarding the intake amount of the food or drink, and based on a predetermined index regarding blood glucose increase due to food or drink; analyze the glucose tolerance of the subject based on the accepted information regarding the amount of glucose and based on the calculated reference value; and control the output section to output an obtained analysis result as an analysis result of glucose tolerance.

19 Claims, 18 Drawing Sheets

(51) Int. Cl.
  *G06G 7/48*    (2006.01)
  *G06G 7/58*    (2006.01)
  *A61B 5/15*    (2006.01)
  *A61B 5/00*    (2006.01)
  *A61B 5/145*   (2006.01)
  *A61B 5/1455*  (2006.01)
  *A61B 5/151*   (2006.01)

(52) U.S. Cl.
  CPC .... *A61B 5/15117* (2013.01); *A61B 5/150412* (2013.01); *A61B 5/150969* (2013.01); *A61B 5/150984* (2013.01); *A61B 5/7475* (2013.01); *A61B 5/6824* (2013.01); *A61B 2560/0456* (2013.01); *A61B 2560/0487* (2013.01)

(56)      References Cited

U.S. PATENT DOCUMENTS

2010/0160758 A1    6/2010   Okada et al.
2011/0034787 A1*   2/2011   Hagino .............. A61B 5/14514
                                                          600/316
2011/0070565 A1    3/2011   Okada et al.

FOREIGN PATENT DOCUMENTS

EP         2 130 487 A1    12/2009
JP         06-027745        2/1994
JP         11-148940        6/1999
JP         2000-131327      5/2000
JP         2001-165752      6/2001
JP         2009-036513      2/2009
JP         2009-150859      7/2009
WO         WO 03/083133 A1  10/2003

* cited by examiner

F I G. 1 1
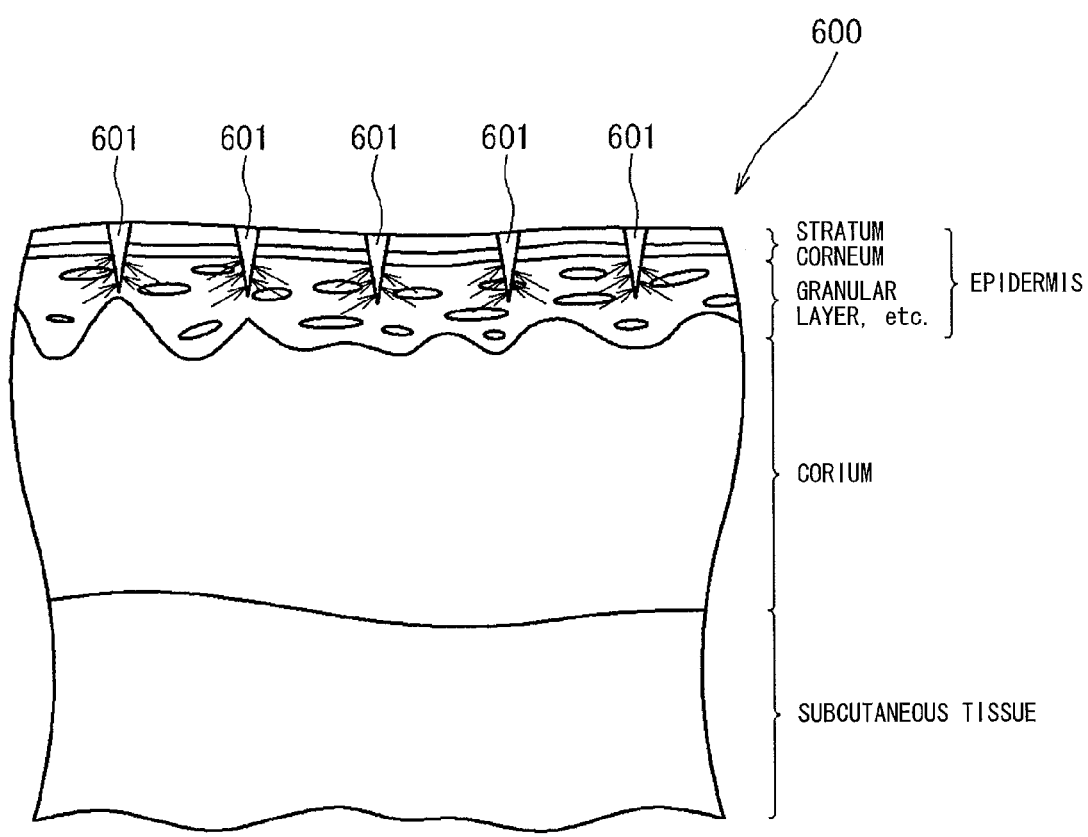

FIG. 15

| MEAL INFORMATION | | | |
|---|---|---|---|
| | DISH NAME | INTAKE AMOUNT | |
| INGESTED FOOD 1 | MEAT SPAGHETTI ▽ | 500 | g |
| INGESTED FOOD 2 | ▽ | | g |
| INGESTED FOOD 3 | ▽ | | g |
| INGESTED FOOD 4 | ▽ | | g |
| INGESTED FOOD 5 | ▽ | | g |

A1 (points to dropdown for Ingested Food 1)
A2 (points to intake amount for Ingested Food 1)

AUC VALUE
A3 — [   ] mg·h/dl ously*

GLUCOSE TOLERANCE ANALYZER, GLUCOSE TOLERANCE ANALYZING SYSTEM, AND STORAGE MEDIUM

RELATED APPLICATIONS

This application claims priority under 35 U.S.C. §119 to Japanese Patent Application No. 2011-227955 filed on Oct. 17, 2011, the entire content of which is hereby incorporated by reference.

BACKGROUND OF THE INVENTION

1. Field of the Invention

The present invention relates to glucose tolerance analyzers, glucose tolerance analyzing systems, and storage media. More specifically, the present invention relates to glucose tolerance analyzers, glucose tolerance analyzing systems, and storage media that are useful for early detection, diagnosis, treatment, and the like of diabetes.

2. Description of the Related Art

For early detection of diabetes, tests are being performed that detect postprandial hyperglycemia, which is a symptom of early stage diabetes and is caused by abnormal glucose tolerance. As a test that detects postprandial hyperglycemia, for example, an oral glucose tolerance test (OGTT) is known. However, an OGTT requires an excessive glucose load, and thus has a disadvantage of posing a great burden to a patient.

Thus, in order to alleviate the burden to a patient, tests for detecting abnormal glucose tolerance are performed based on the amounts of myo-inositol in urine before and after a glucose load is given (for example, see International Publication WO 2003/083133).

However, myo-inositol in urine is a metabolic product of sugar, and is not an index that directly corresponds to a blood glucose level. Therefore, the method described in International Publication WO2003/083133 has a disadvantage that the diagnostic accuracy is not sufficient. Further, since the method requires a glucose load, the method has a problem that it poses a great burden to a patient.

The present invention has been made in view of the above situations. An object of the present invention is to provide a glucose tolerance analyzer, a glucose tolerance analyzing system, and a storage medium that allow alleviation of burden to a patient at the time of glucose tolerance analysis, and that allow simple and highly accurate glucose tolerance analysis.

SUMMARY OF THE INVENTION

The scope of the present invention is defined solely by the appended claims, and is not affected to any degree by the statements within this summary.

A first aspect of the present invention is a glucose tolerance analyzer comprising: an accepting section configured to accept inputs of information regarding a type of food or drink ingested by a subject, information regarding an intake amount of the food or drink, and information regarding an amount of glucose in the subject after the ingestion of the food or drink; an output section configured to output an analysis result of glucose tolerance; and a controller configured to: calculate a reference value for analyzing glucose tolerance of the subject based on the accepted information regarding the type of the food or drink ingested by the subject and the accepted information regarding the intake amount of the food or drink, and based on a predetermined index regarding blood glucose increase due to food or drink; analyze the glucose tolerance of the subject based on the accepted information regarding the amount of glucose and based on the calculated reference value; and control the output section to output an obtained analysis result as an analysis result of glucose tolerance.

A second aspect of the present invention is a glucose tolerance analyzing system, comprising: a first information processing apparatus and a second information processing apparatus, wherein the first information processing apparatus comprises: an accepting section configured to accept inputs of information regarding a type of food or drink ingested by a subject, information regarding an intake amount of the food or drink, and information regarding an amount of glucose in the subject after the ingestion of the food or drink; a first transmission section configured to transmit the information accepted by the accepting section, to the second information processing apparatus; a first reception section configured to receive an analysis result of glucose tolerance of the subject from the second information processing apparatus; and an output section configured to output the analysis result received by the first reception section, and the second information processing apparatus comprises: a second reception section configured to receive the information transmitted from the first transmission section; a controller configured to calculate a reference value for analyzing the glucose tolerance of the subject based on the received information regarding the type of the food or drink ingested by the subject and the received information regarding the intake amount of the food or drink, and based on a predetermined index regarding blood glucose increase due to food or drink, and configured to analyze the glucose tolerance of the subject based on the received information regarding the amount of glucose received by the second reception section and based on the calculated reference value; and a second transmission section configured to transmit an analysis result obtained by the controller to the first information processing apparatus.

A third aspect of the present invention is a glucose tolerance analyzing method, comprising: an accepting step of accepting inputs of information regarding a type of food or drink ingested by a subject, information regarding an intake amount of the food or drink, and information regarding an amount of glucose in the subject after the ingestion of the food or drink; an output step of outputting an analysis result of glucose tolerance; and a control step of: calculating a reference value for analyzing glucose tolerance of the subject based on the accepted information regarding the type of the food or drink ingested by the subject and the accepted information regarding the intake amount of the food or drink, and based on a predetermined index regarding blood glucose increase due to food or drink; analyzing the glucose tolerance of the subject based on the accepted information regarding the amount of glucose and based on the calculated reference value; and controlling an obtained analysis result to be outputted in the output step as an analysis result of glucose tolerance.

A forth aspect of the present invention is a non-transitory storage medium having stored thereon computer-executable programs executed by at least one processor of a computer system which is connected to an output device and an input device, the programs controlling the at least one processor to perform the steps of: controlling an accepting section to accept, via the input device, inputs of information regarding a type of food or drink ingested by a subject, information regarding an intake amount of the food or drink, and information regarding an amount of glucose in the subject after the ingestion of the food or drink; calculating a reference value for analyzing glucose tolerance of the subject based on the accepted information regarding the type of the food or drink ingested by the subject and the accepted information regarding the intake amount of the food or drink, and based on a predetermined index regarding blood glucose increase due to food or drink; analyzing the glucose tolerance of the subject based on the accepted information regarding the amount of glucose accepted by the accepting section and based on the calculated reference value; and controlling the output device to output an obtained analysis result.

BRIEF DESCRIPTION OF THE DRAWINGS

FIG. 11 is a cross-sectional view illustrating a skin in which micropores are formed by the micropore forming device;

FIG. 15 shows one example of an input screen;

DETAILED DESCRIPTION OF THE PREFERRED EMBODIMENTS

The preferred embodiments of the present invention will be described hereinafter with reference to the drawings.

Embodiment 1

The present embodiment is a glucose tolerance analyzing system in which: a terminal (first information processing apparatus) which accepts inputs of information regarding the type of food or drink ingested by a subject, information regarding the intake amount of the food or drink, and information regarding the amount of glucose in the subject after the ingestion of the food or drink, and which outputs an analysis result; and a server (second information processing apparatus) which stores indices regarding blood glucose increase due to food or drink and a calculation formula for calculating a reference value for analyzing the glucose tolerance of the subject, which calculates a reference value for analyzing the glucose tolerance of the subject, and which analyzes the glucose tolerance of the subject, are communicably connected to each other via a network.

[Overall Configuration of Glucose Tolerance Analyzing System]

Figure 1:
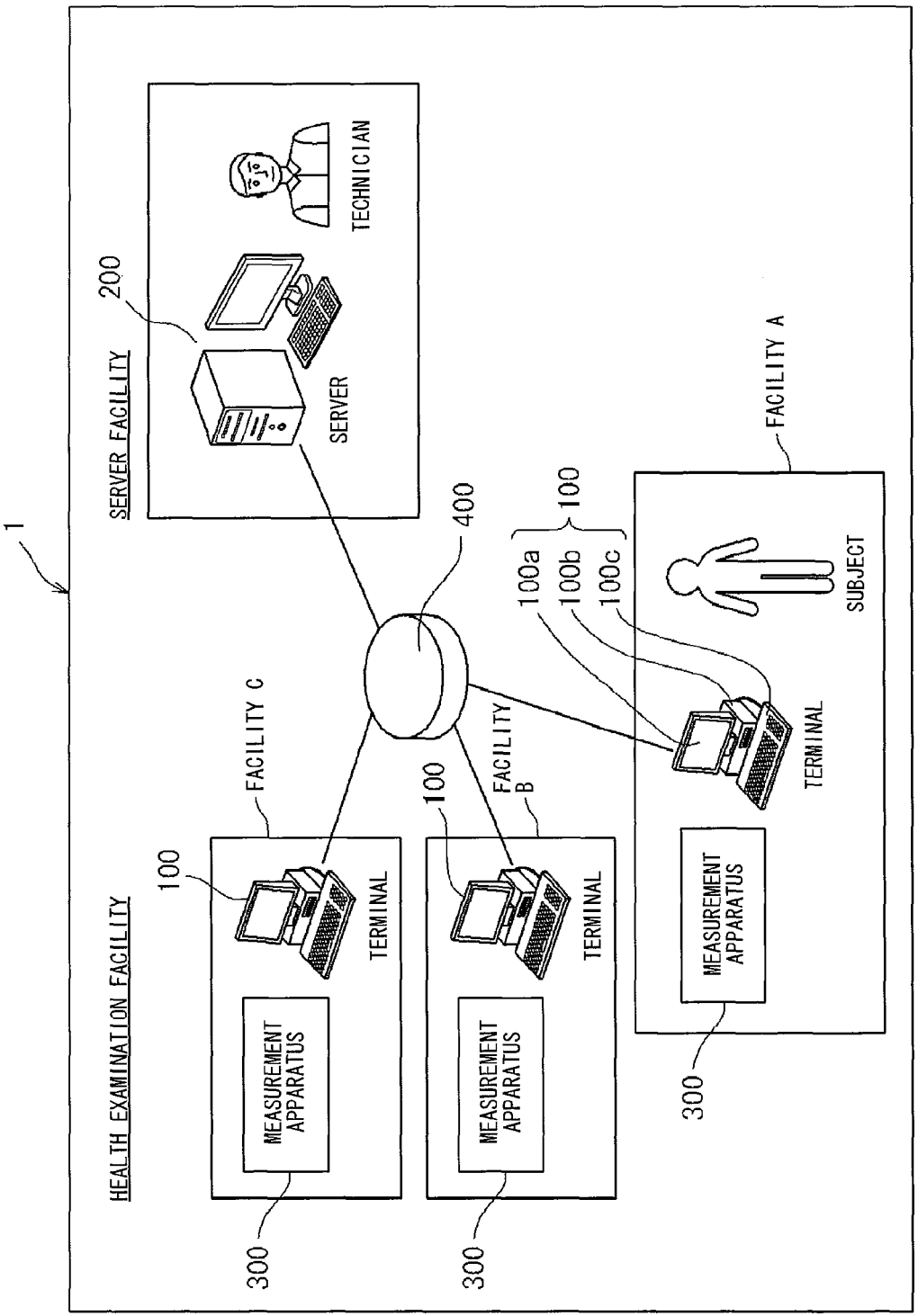
FIG. 1 is a schematic diagram illustrating a glucose tolerance analyzing system according to one embodiment of the present invention.

FIG. 1 is a schematic diagram illustrating a glucose tolerance analyzing system according to one embodiment of the present invention.

As shown in FIG. 1, a glucose tolerance analyzing system 1 includes terminals 100 (first information processing apparatus) respectively installed in facilities A to C, a server 200 (second information processing apparatus) installed in a server facility, and a network 400 such as the Internet.

Each terminal 100 and the server 200 are communicably connected to each other via the network 400.

A measurement apparatus 300 which measures a blood glucose AUC of a subject is installed in each of the facilities. A blood glucose AUC of a subject is information regarding the amount of glucose in the subject after ingestion of food or drink.

It should be noted that a plurality of the terminals 100 may be installed in one facility.

[Configuration of Terminal (First Information Processing Apparatus)]

Figure 2:
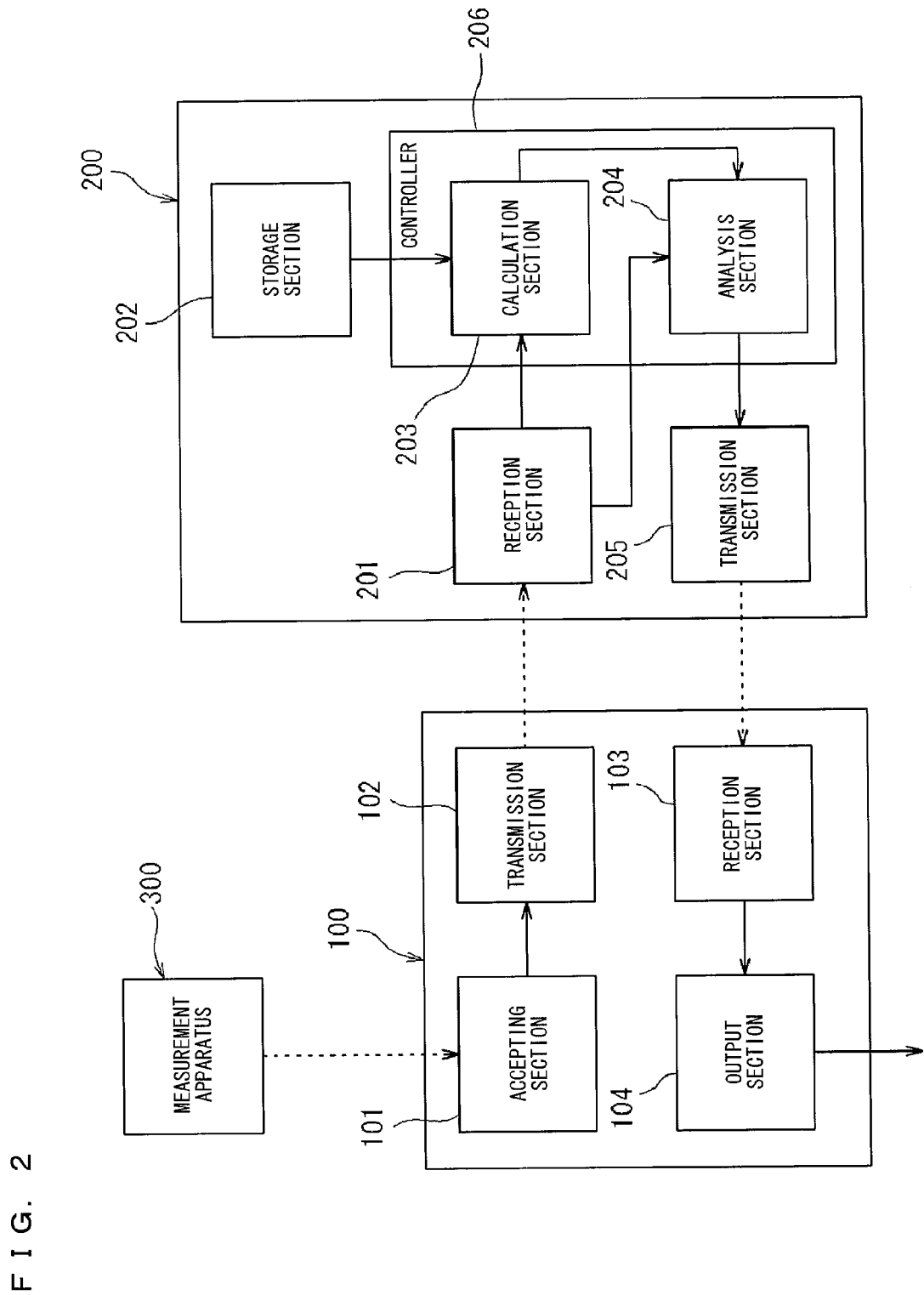
FIG. 2 is a block diagram showing a functional configuration of the glucose tolerance analyzing system shown in FIG. 1.

As shown in FIG. 2, the terminal 100 includes an accepting section 101, a transmission section 102, a reception section 103, and an output section 104. The accepting section 101 accepts inputs of information regarding the type of food or drink ingested by a subject, information regarding the intake amount of the food or drink, and information regarding the amount of glucose in the subject after the ingestion of the food or drink. The transmission section 102 transmits the information accepted by the accepting section 101, to the server 200. The reception section 103 receives information (analysis result) obtained by the server 200. The output section outputs the information (analysis result) received by the reception section 103.

Figure 3:
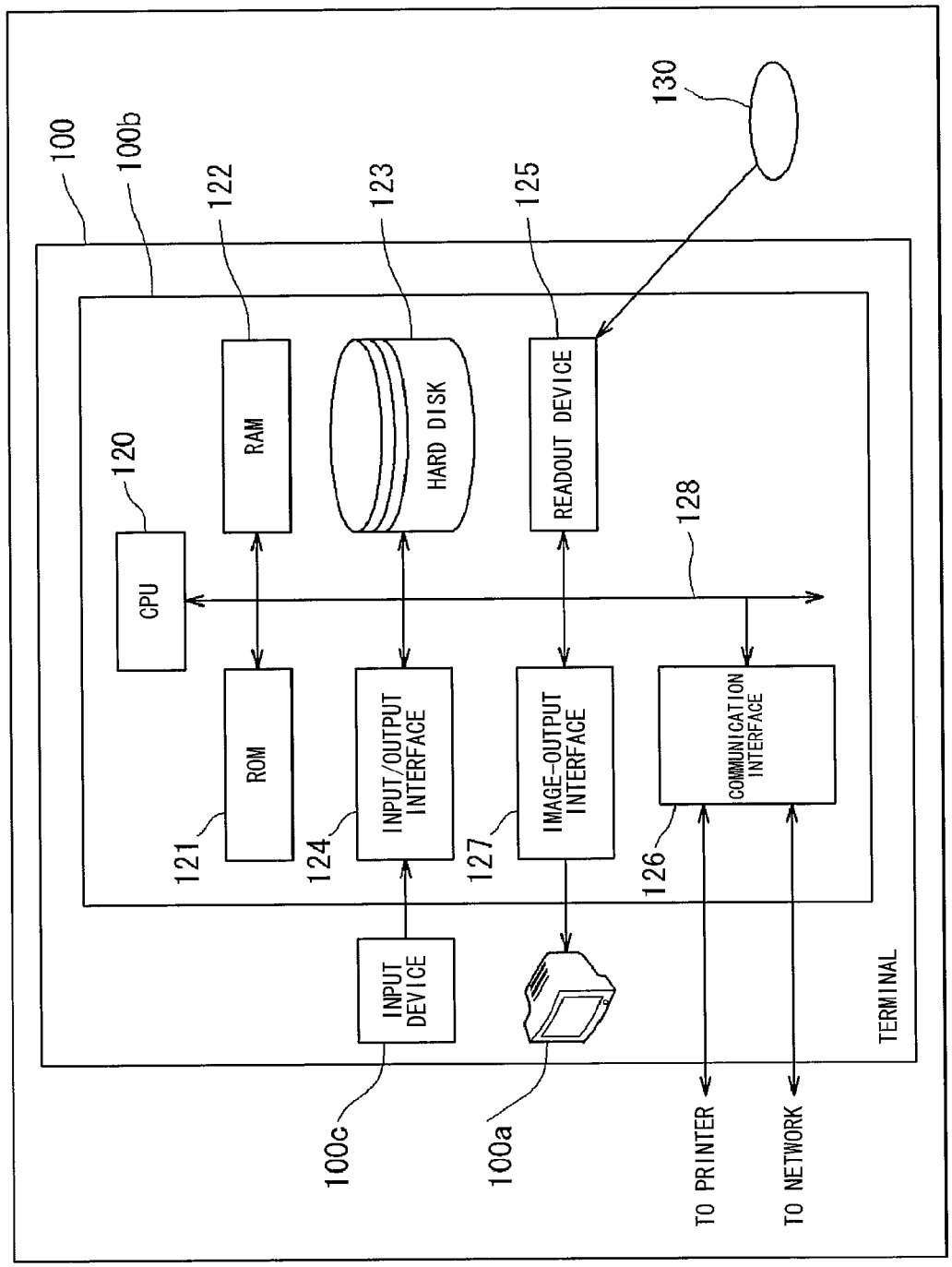
FIG. 3 is a block diagram showing a hardware configuration of a terminal included in the glucose tolerance analyzing system shown in FIG. 1.

FIG. 3 is a block diagram showing a hardware configuration of the terminal 100.

As shown in FIG. 3, the terminal 100 is a computer including a display 100a, a body 100b, and an input device 100c. The body 100b includes a CPU (Central Processing Unit) 120, a ROM (Read Only Memory) 121, a RAM 122, a hard disk 123, an input/output interface 124, a readout device 125, a communication interface 126, and an image-output interface 127. The CPU 120, the ROM 121, the RAM (Random Access Memory) 122, the hard disk 123, the input/output interface 124, the readout device 125, the communication interface 126, and the image-output interface 127 are data-communicably connected to each other via a bus 128.

The CPU 120 can execute computer programs stored in the ROM 121 and computer programs loaded onto the RAM 122. By the CPU 120 executing application programs, the functional blocks described above are realized. Accordingly, the computer functions as a terminal being a first information processing apparatus in the glucose tolerance analyzing system 1.

The ROM 121 is implemented by a mask ROM, PROM, EPROM, EEPROM, or the like. The ROM 121 stores computer programs executed by the CPU 120 and data used by them.

The RAM 122 is implemented by a SRAM, DRAM, or the like. The RAM 122 is used for reading out computer programs stored in the ROM 121 and the hard disk 123. The RAM 122 is also used as a work area for the CPU 120 when the CPU 120 executes these computer programs.

An operating system to be executed by the CPU 120, computer programs such as application programs, and data used for execution of the computer programs are installed in the hard disk 123.

The readout device 125 is implemented by a flexible disk drive, CD-ROM drive, DVD-ROM drive, or the like. The readout device 125 can read out computer programs or data stored in a portable storage medium 130.

The input/output interface 124 is implemented by, for example, a serial interface such as USB, IEEE1394, and RS-232C, a parallel interface such as SCSI, IDE, and IEEE1284, and an analog interface such as a D/A converter and an A/D converter. The input device 100c such as a keyboard, a mouse, and the like is connected to the input/output interface 124. An operator can input data to the body 100b by using the input device 100c.

The communication interface 126 is, for example, Ethernet (registered-trademark) interface. The communication interface 126 allows the terminal 100 to transmit/receive data to/from the server 200 connected thereto via the network 400, by using a predetermined communication protocol. Further, the communication interface 126 allows the terminal 100 to transmit print data to a printer.

The image-output interface 127 is connected to the display 100a implemented by an LCD, CRT, or the like. Accordingly, the display 100a can output video signals corresponding to image data provided by the CPU 120. The display 100a displays an image (screen) in accordance with the inputted video signals.

[Configuration of Server (Second Information Processing Apparatus)]

As shown in FIG. 2, the server 200 includes a reception section 201, a storage section 202, a calculation section 203, an analysis section 204, and a transmission section 205. The reception section 201 is communicably connected to the transmission section 102 of the terminal 100 via the network 400. The calculation section 203 and the analysis section 204 constitute a controller 206.

The reception section 201 receives information transmitted from the transmission section 102 of the terminal 100. The storage section 202 stores predetermined indices regarding blood glucose increase due to food or drink, and a calculation formula for calculating a reference value for analyzing the glucose tolerance of a subject. The calculation section 203 calculates a reference value for analyzing the glucose tolerance of a subject based on the information regarding the type of food or drink ingested by the subject and the information regarding the intake amount of the food or drink, which were received by the reception section 201, and based on the indices stored in the storage section 202, in accordance with the calculation formula stored in the storage section 202. The analysis section 204 analyzes the glucose tolerance of the subject based on the information regarding the amount of glucose received by the reception section 201 and based on the reference value calculated by the calculation section 203. The transmission section 205 is communicably connected to the reception section 103 of the terminal 100 via the network 400. The transmission section 205 transmits an analysis result obtained by the analysis section 204 to the terminal 100.

Figure 4:
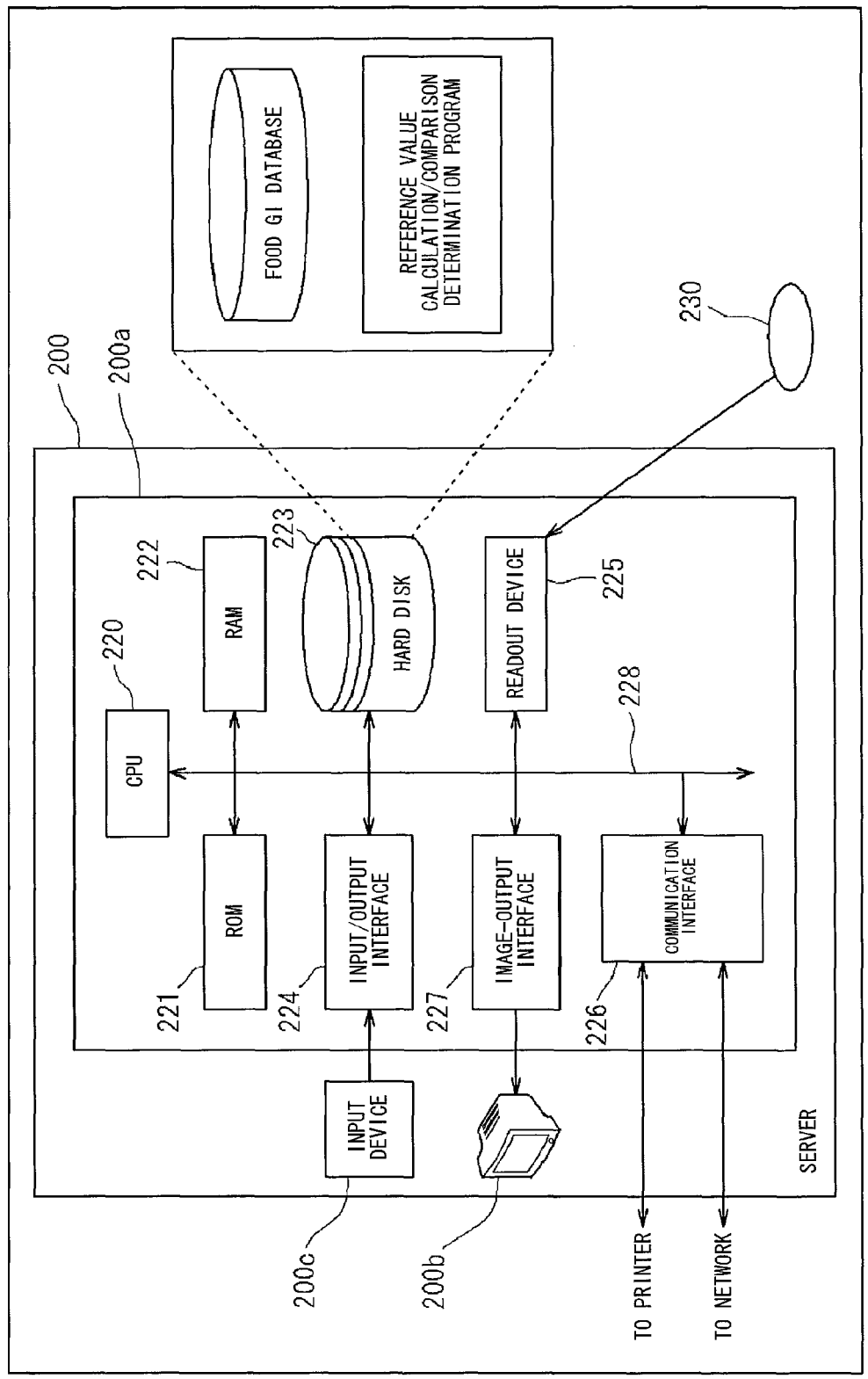
FIG. 4 is a block diagram showing a hardware configuration of a server included in the glucose tolerance analyzing system shown in FIG. 1.

FIG. 4 is a block diagram showing a hardware configuration of the server 200.

As shown in FIG. 4, the server 200 is a computer including a body 200a, a display 200b, and an input device 200c.

The body 200a includes a CPU 220, a ROM 221, a RAM 222, a hard disk 223, an input/output interface 224, a readout device 225, a communication interface 226, and an image-output interface 227. The CPU 220, the ROM 221, the RAM 222, the hard disk 223, the input/output interface 224, the readout device 225, the communication interface 226, and the image-output interface 227 are data-communicably connected to each other by a bus 228.

The CPU 220 can execute computer programs stored in the ROM 221 and computer programs loaded onto the RAM 222. By the CPU 220 executing application programs, the functional blocks described above are realized, whereby the computer functions as the server 200.

The ROM 221 is implemented by a mask ROM, PROM, EPROM, EEPROM, or the like. The ROM 221 stores computer programs executed by the CPU 220, and data and the like used by them.

The RAM 222 is implemented by a SRAM, DRAM, or the like. The RAM 222 is used for reading out computer programs stored in the ROM 221 and the hard disk 223. The RAM 222 is also used as a work area for the CPU 220 when the CPU 220 executes these computer programs.

An operating system to be executed by the CPU 220, computer programs such as application programs, and data used for execution of the computer programs are installed in the hard disk 223.

In the hard disk 223, for example, an operating system that provides a graphical user interface environment for Windows (registered-trademark) manufactured and sold by Microsoft corp. is installed. In the description below, it is assumed that application programs according to the present embodiment operate on this operating system.

Further, in a predetermined area of the hard disk 223, a GI database of food or drink as indices regarding blood glucose increase due to food or drink, and application programs such as a reference value calculation/comparison determination program are stored.

Figure 5:
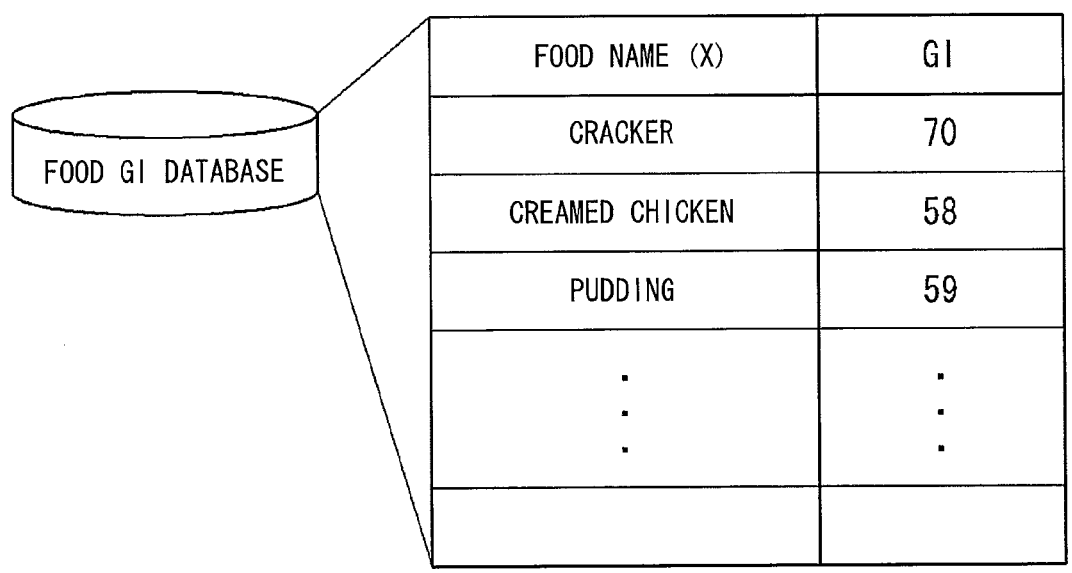
FIG. 5 is a diagram illustrating one example of a GI (Glycemic Index) database of food or drink stored in a hard disk of the server shown in FIG. 4.

As shown in FIG. 5, types of food or drink (food name) and glycemic indices (GI) of food or drink are stored associated with each other, in the GI database of food or drink.

The reference value calculation/comparison determination program calculates a reference value for analyzing the glucose tolerance of the subject based on the information regarding the type of food or drink ingested by the subject and the information regarding the intake amount of the food or drink, which were received from the terminal 100, and based on the GI database of food or drink, in accordance with a predetermined calculation formula, and analyzes the glucose tolerance of the subject based on the information regarding the amount of glucose received from the terminal 100 and based on the calculated reference value.

The input/output interface 224 is implemented by, for example, a serial interface such as USB, IEEE1394, and RS-232C, a parallel interface such as SCSI, IDE, and IEEE1284, and an analog interface such as a D/A converter and an A/D converter. The input device 200c such as a keyboard, a mouse, and the like is connected to the input/output interface 224. An operator can input data to the body 200a by using the input device 200c.

The readout device 225 is implemented by a flexible disk drive, CD-ROM drive, DVD-ROM drive, or the like. The readout device 225 can read out computer programs or data stored in a portable storage medium 230.

The communication interface 226 is, for example, Ethernet (registered-trademark) interface. The communication interface 226 allows the server 200 to transmit/receive data to/from the terminal 100 connected thereto via the network 400, by using a predetermined communication protocol. The communication interface 226 allows the server 200 to transmit print data to a printer.

The image-output interface 227 is connected to the display 200b implemented by an LCD, CRT, or the like. Accordingly, the display 200b can output video signals corresponding to image data provided by the CPU 220. The display 200b displays an image (screen) in accordance with the inputted video signals.

It should be noted that the GI database may not necessarily be stored in the hard disk 223. For example, the server 200 may download the GI database from a communication network via the communication interface 226.

[Configuration of Measurement Apparatus]

Figure 6:
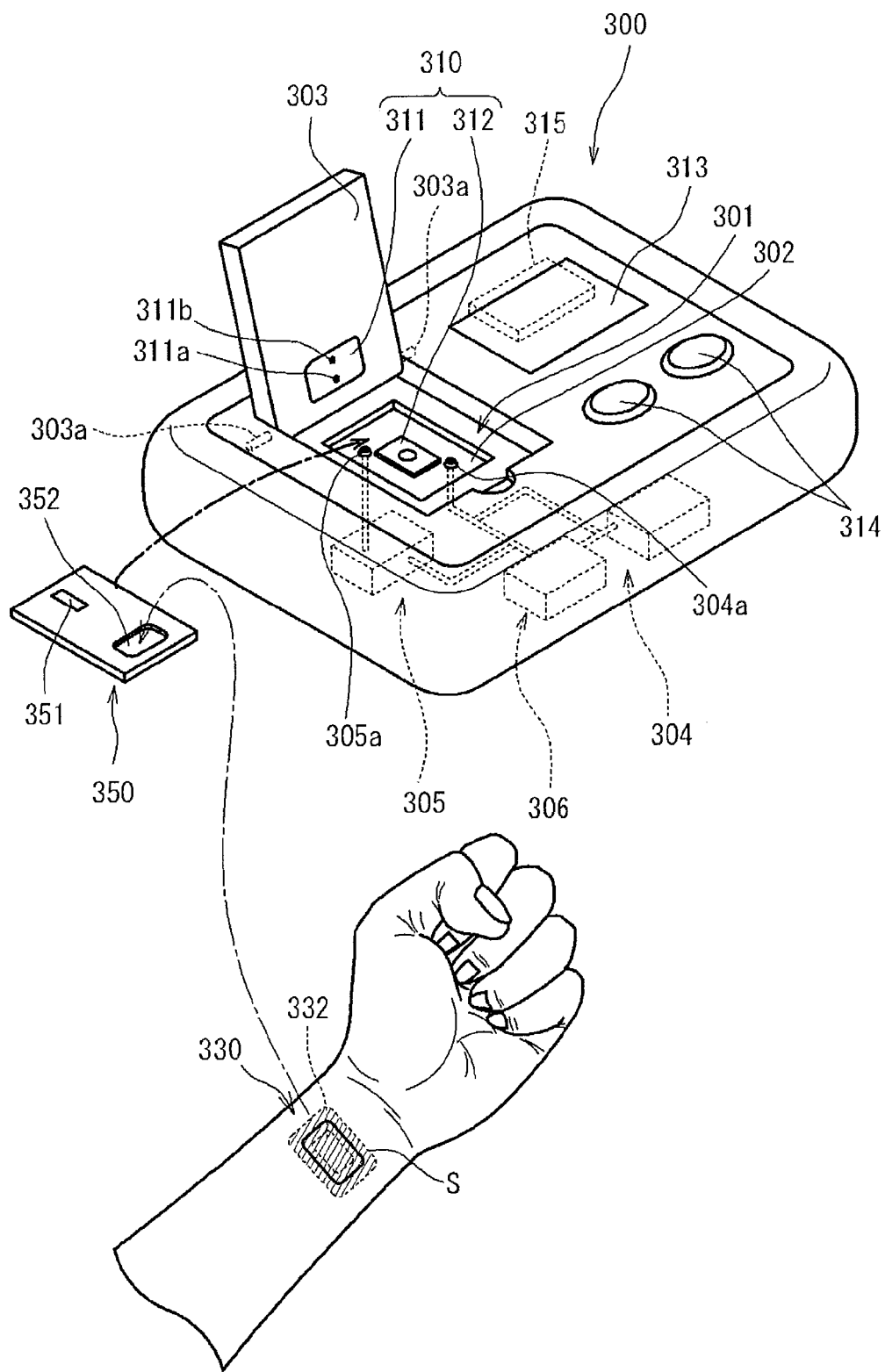
FIG. 6 is a perspective view illustrating one example of a measurement apparatus for obtaining a blood glucose AUC value as information regarding the amount of glucose in a subject after ingestion of food or drink.
Figure 7:
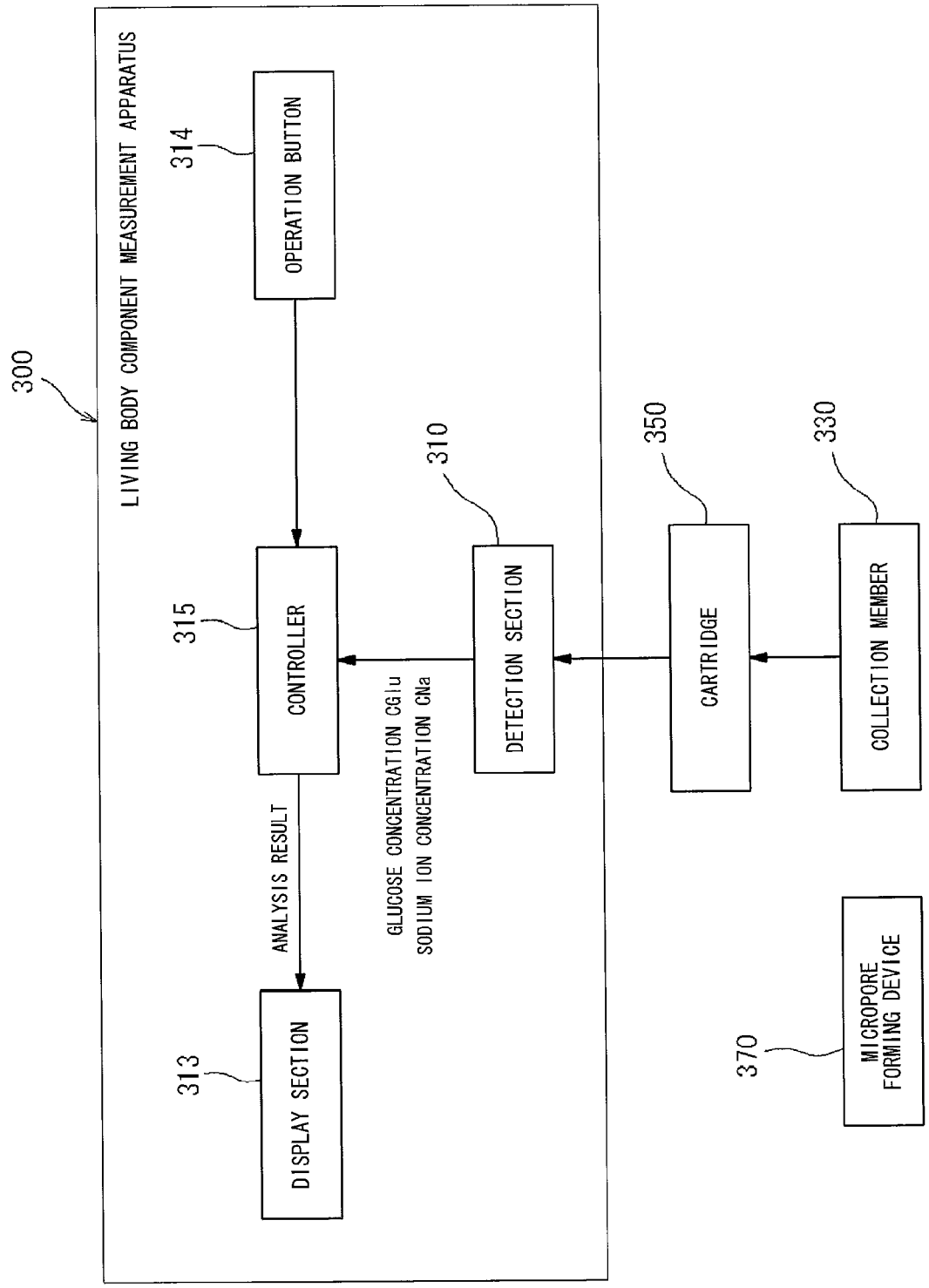
FIG. 7 is a block diagram showing a functional configuration of the measurement apparatus shown in FIG. 6.

FIG. 6 is a perspective view illustrating an external appearance of one example of a measurement apparatus for obtaining a blood glucose AUC value as information regarding the amount of glucose in a subject after ingestion of food or drink. FIG. 7 is a block diagram of the measurement apparatus 300 shown in FIG. 6.

The measurement apparatus 300 shown in FIG. 6 is an apparatus that measures glucose and sodium ion contained in tissue fluid collected in a collector 332 of a collection member 330, obtains a glucose concentration (CGIu) and a sodium ion concentration (CNa), calculates an estimated blood glucose AUC of the subject based on the obtained CGlu and CNa, generates an analysis result including the estimated blood glucose AUC, and displays the analysis result. The measurement apparatus 300 includes a detection section 310, a controller 315 including an analysis section, a display section 313 for displaying an analysis result and the like, and an operation button 314 for issuing an instruction to start measurement, and the like.

The measurement apparatus 300 includes a thick rectangular parallelepiped-shaped housing. A recess 301 is formed in a top plate on the upper face of the housing. The recess 301 is provided with a cartridge placement part 302 which is a recess formed in a deeper level than the recess 301. Further, the recess 301 is coupled with a movable top plate 303 having substantially the same thickness as the height of side walls of the recess 301. By rotating about a supporting shaft 303a, the movable top plate 303 can be housed in the recess 301 from the state shown in FIG. 6, or can be held upright as shown in FIG. 6 from a state where the movable top plate 303 is housed in the recess 301. The cartridge placement part 302 is large enough to house a cartridge 350 described below.

The movable top plate 303 is supported by the supporting shaft 303a so as to be able to fall down to be housed in the recess 301. Accordingly, the cartridge 350 placed in the cartridge placement part 302 is pressed from above by the movable top plate 303.

The detection section 310 obtains information of components contained in the tissue fluid collected in the collector 332 of the collection member 330. The detection section 310 includes a glucose detector 311 which detects a glucose concentration CGlu, glucose being a component to be measured, and a sodium ion detector 312 which detects a sodium ion concentration CNa.

The glucose detector 311 is provided on a back face of the movable top plate 303, that is, on a face that faces the cartridge placement part 302 when the movable top plate 303 is housed in the recess 301. The glucose detector 311 includes a light source 311a for emitting light, and a light receiver 311b for receiving reflected light of light emitted by the light source 311a. Accordingly, the glucose detector 311 can emit light to the cartridge 350 placed in the cartridge placement part 302, and can receive reflected light from the cartridge 350 which has been irradiated.

The sodium ion detector 312 is provided on the bottom face of the cartridge placement part 302. The sodium ion detector 312 includes a rectangular plate-like member provided on the bottom face of the cartridge placement part 302. A pair of sodium ion concentration measurement electrodes is provided at substantially the center of the plate-like member. The sodium ion concentration measurement electrodes include a sodium ion selective electrode which is made of silver/silver chloride and which includes a sodium ion selective membrane, and a silver/silver chloride electrode which is a counter electrode.

The controller 315 is provided within the measurement apparatus 300, and includes a CPU being an analysis section, and a ROM, RAM, and the like being a storage section. By reading out and executing programs stored in the ROM, the CPU controls operations of the components. The RAM is used as an area where a program stored in the ROM is loaded to be executed.

The measurement apparatus 300 includes a supply part 304 which includes a pump, a tank 306 for storing recovery fluid which is pure water for recovering the tissue fluid collected in the collector 332 of the collection member 330, and a waste fluid tank 305 for storing waste fluid. The supply part 304 sends air to the tank 306, and thereby injects, through a nipple 304a, the recovery fluid stored in the tank 306 into the cartridge 350 placed in the cartridge placement part 302.

The waste fluid tank 305 is a mechanism into which the pure water sent by the supply part 304 to the cartridge 350 is discharged. The waste fluid tank 305 stores fluid discharged thereinto through a nipple 305a.

Figure 8:
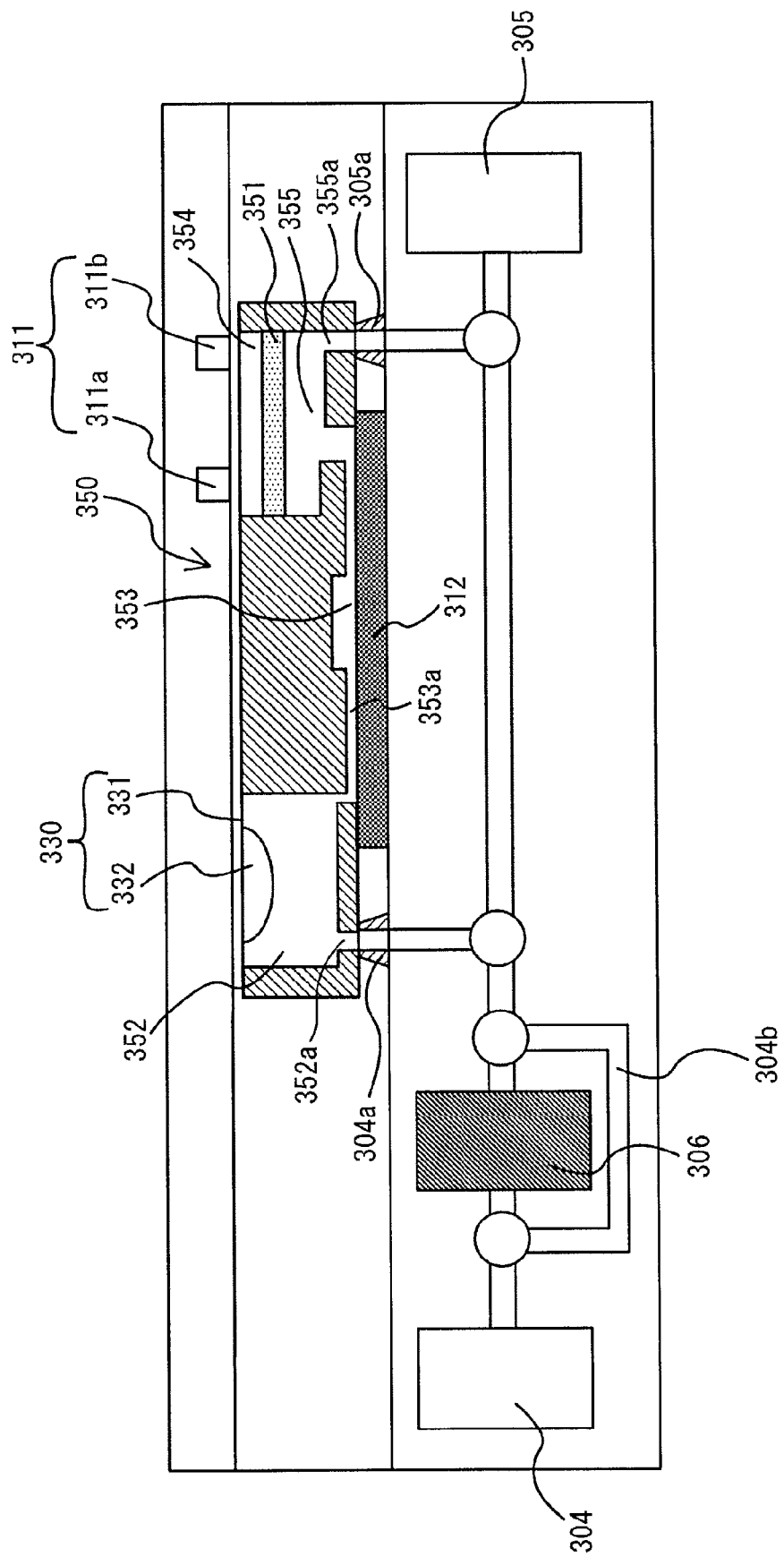
FIG. 8 is a schematic cross-sectional view showing a configuration of a cartridge.

FIG. 8 is a schematic cross-sectional view showing a state where the cartridge 350 is placed in the cartridge placement part 302.

The cartridge 350 includes a gel storing part 352, a glucose reactant 351, and an optical waveguide member 354. The gel storing part 352 is a recess formed in a surface of the cartridge 350. On the bottom of the gel storing part 352, an injection hole 352a which communicates with the nipple 304a provided in the cartridge placement part 302 is provided. A groove that communicates with the gel storing part 352 is formed on the lower face of the cartridge 350. The groove and the sodium ion detector 312 provided at the bottom of the cartridge placement part 302 forms a flow path 353a. Part of the flow path 353a serves as a first reservoir 353 where the sodium ion detector 312 detects a sodium ion concentration. The downstream of the flow path 353a communicates with a second reservoir 355. The second reservoir 355 is formed as a recess provided in a surface of the cartridge 350, and its opening is closed with the optical waveguide member 354 having an optical waveguide. The glucose reactant 351 which reacts with glucose and thereby changes its color is provided on the lower face of the optical waveguide member 354. A discharging hole 355a, which communicates with the nipple 305a provided in the cartridge placement part 302, is provided at the bottom of the second reservoir 355.

The measurement apparatus 300 measures a glucose concentration CGlu and a sodium ion concentration CNa in the tissue fluid collected by the collection member 330 in a manner described below. First, as indicated by the dashed-dotted line in FIG. 6, the collection member 330 which has been attached to a skin S of a subject for a predetermined time period is removed from the skin, and then attached to the gel storing part 352 of the cartridge 350. The cartridge 350 is placed in the cartridge placement part 302 of the measurement apparatus 300, and then, the movable top plate 303 is closed.

When an instruction to start measurement is issued by means of the operation button 314, air is supplied from the supply part 304 to the tank 306, and the recovery fluid is sent from the tank 306 to the nipple 304a. The recovery fluid is injected from the injection hole 352a into the gel storing part 352, and the gel storing part 352 is filled with the recovery fluid. In this state, the tissue fluid collected in the collector 332 disperses into the recovery fluid over a predetermined time period. After a predetermined time period has elapsed, the supply part 304 sends air into the gel storing part 352 through a bypass 304b. Accordingly, the fluid in the gel storing part 352 is sent to the first reservoir 353 and to the second reservoir 355, through the flow path 353a.

The sodium ion detector 312 applies a constant voltage to the fluid reserved in the first reservoir 353 via the sodium ion concentration measurement electrodes, to obtain a current value. The current value at this time is proportionate to the sodium ion concentration in the fluid. The sodium ion detector 312 outputs the obtained current value as a detection signal to the controller 315. The controller 315 obtains a sodium ion concentration CNa based on the current value contained in the detection signal and on a calibration curve stored in advance in the storage section of the controller 315.

In the second reservoir, glucose in the recovery fluid reacts with the glucose reactant 351, and the color of the glucose reactant 351 changes. The glucose detector 311 emits light from the light source 311a to the optical waveguide member 354, and receives by the light receiver 311b light emitted from the optical waveguide member 354. When light is emitted from the light source 311a, the light travels while being absorbed by the discolored glucose reactant 351 and being repeatedly reflected within the optical waveguide member 354, and then enters the light receiver 311b. The amount of light received by the light receiver 311b is proportionate to the degree of discoloration of the glucose reactant 351, and the degree of discoloration is proportionate to the amount of glucose in the recovery fluid. The glucose detector 311 outputs, to the controller 315, the obtained amount of received light as a detection signal. The controller 315 obtains a glucose concentration CGlu, based on the amount of received light contained in the detection signal and a calibration curve stored in advance in the storage section of the controller 315.

When the sodium ion concentration CNa and the glucose concentration CGlu are obtained, air is further sent from the supply part 304 into the cartridge 350. Accordingly, the recovery fluid is sent to the waste fluid tank 305 through the discharging hole 355a and the nipple 305a, and the series of the measurement ends.

[Configuration of Micropore Forming Device]

Next, one example of a micropore forming device (puncture tool) for forming micropores in the skin of a subject will be described. The micropore forming device is an apparatus that forms a large number of micropores in a part of the skin of a subject, thereby promoting extraction of tissue fluid from the skin of the subject. In the present embodiment, glucose and sodium ion are collected from the skin S (see FIG. 6) of a subject in which micropores for promoting extraction of tissue fluid are formed.

Figure 9:
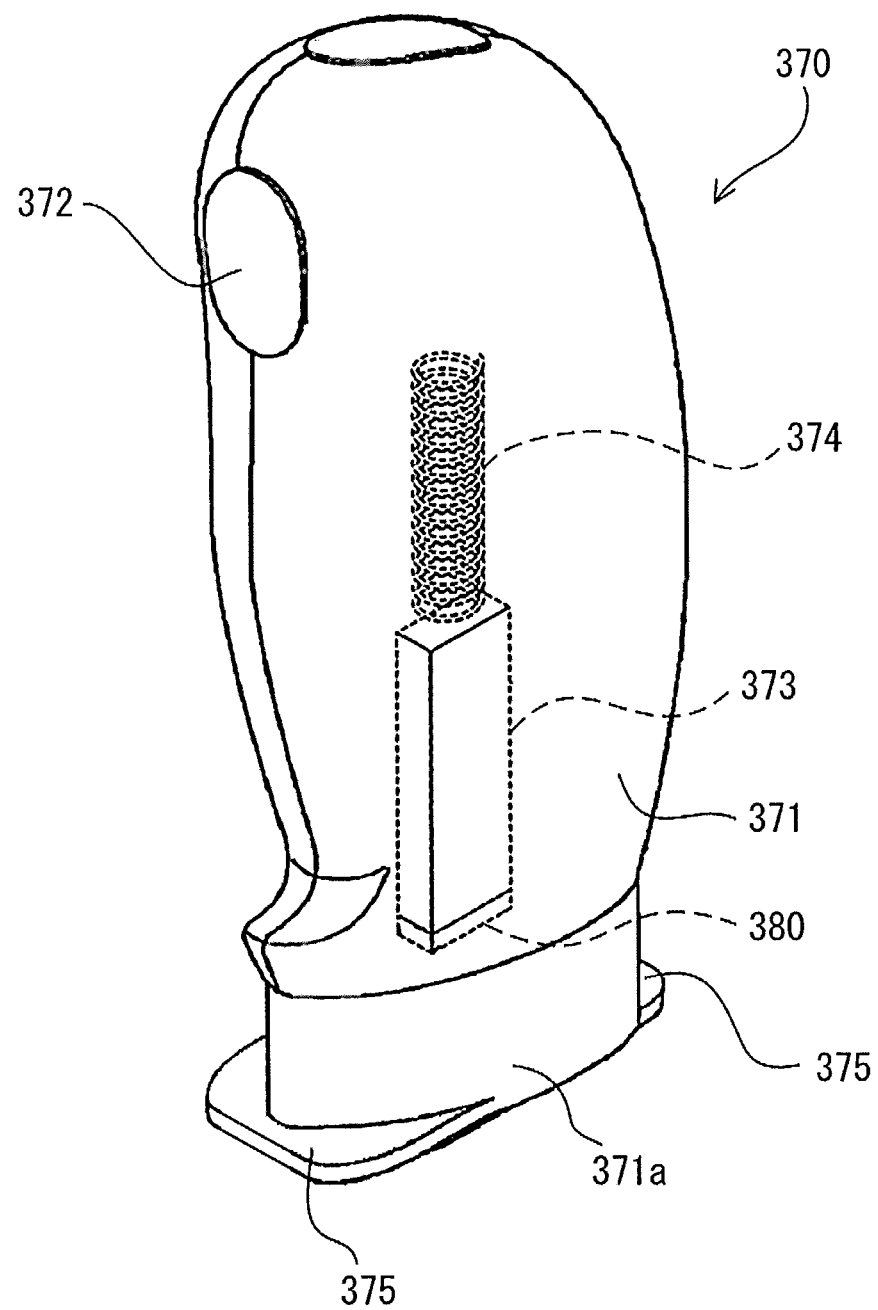
FIG. 9 is a perspective view illustrating one example of a micropore forming device which forms micropores in the skin of a subject.
Figure 10:
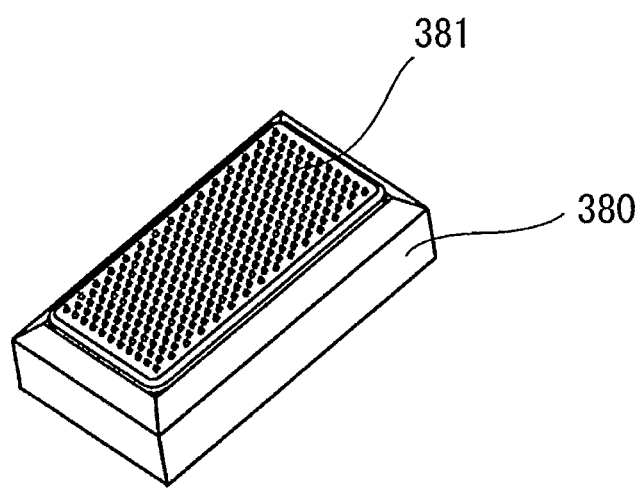
FIG. 10 is a perspective view of a microneedle chip attached to the micropore forming device shown in FIG. 9.

FIG. 9 is a perspective view illustrating a micropore forming device 370 used for forming, in the skin of a subject, micropores for promoting extraction of tissue fluid. FIG. 10 is a perspective view of a microneedle chip 380 attached to the micropore forming device 370 shown in FIG. 9. FIG. 11 is a cross-sectional view illustrating the skin S in which micropores are formed by the micropore forming device 370.

As shown in FIG. 9 to FIG. 11, the micropore forming device 370 is an apparatus that forms holes (micropores 601) for extracting tissue fluid in a skin 600 of a subject, by having a sterilized microneedle chip 380 attached thereto, and by causing microneedles 381 of the microneedle chip 380 to contact with the epidermis of a living body (the skin 600 of the subject). The microneedles 381 of the microneedle chip 380 are caused to contact with the skin such that when the micropores 601 are formed by the micropore forming device 370, the micropores 601 extend within the epidermis of the skin 600 but do not reach the corium.

Further, microscopically, each microneedle 381 has a shape of a frustum of cone. However, the length and the diameter of the tip of the microneedle 381 can be selected as appropriate, in consideration of, for example, the thickness of a membrane provided on the skin of the subject. The microneedle 381 is not limited in particular in the present invention. Typically, the length thereof is about 100 μm to 1000 μm, and the diameter of the tip thereof is about 1 μm to 50 μm.

As shown in FIG. 9, the micropore forming device 370 includes a housing 371, a release button 372 provided on a surface of the housing 371, and an array chuck 373 and a spring member 374 provided inside the housing 371. An opening (not shown) which allows the microneedle chip 380 to pass therethrough is formed in the lower end face (i.e., the face to come into contact with the skin) of a lower part 371a of the housing 371. The spring member 374 has a function of pushing the array chuck 373 in the puncturing direction. The microneedle chip 380 can be attached to the lower end of the array chuck 373. Multiple microneedles 381 are formed on the lower face of the microneedle chip 380. The lower face of the microneedle chip 380 has a size of 10 mm (longer side)×5 mm (shorter side). The micropore forming device 370 has a fixing mechanism (not shown) for fixing the array chuck 373 in a state of being lifted upward (i.e., in a direction opposite to the puncturing direction) against the pushing force of the spring member 374. When a user (subject) presses the release button 372, the fixed state of the array chuck 373 by the fixing mechanism is canceled, and the pushing force of the spring member 374 moves the array chuck 373 in the puncturing direction. As a result, the microneedles 381 of the microneedle chip 380 projecting from the above-described opening puncture the skin. It should be noted that, in FIG. 9, reference numeral 375 denotes a flange formed in the lower part 371*a* of the housing 371. When the micropore forming device 370 is used, the back face of the flange 375 is caused to contact with a predetermined portion of the skin of the subject.

[Configuration of Collection Member]

The collection member 330 is attached to the skin of a subject in order to collect tissue fluid from the skin of the subject, and is removed from the skin after a predetermined time period has elapsed.

Figure 12:
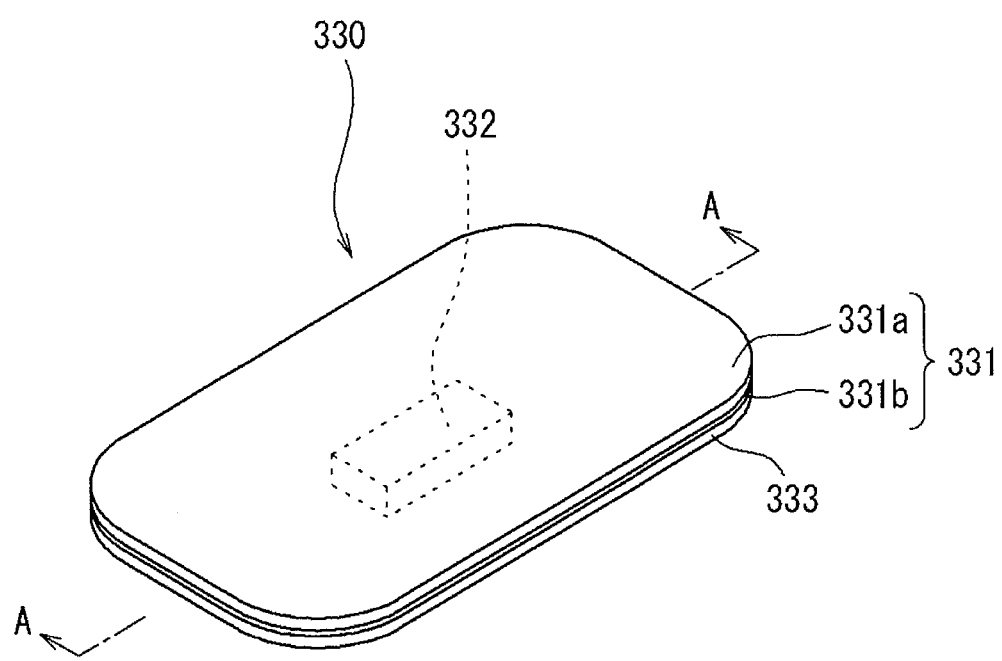
FIG. 12 is a perspective view illustrating one example of a collection member.
Figure 13:
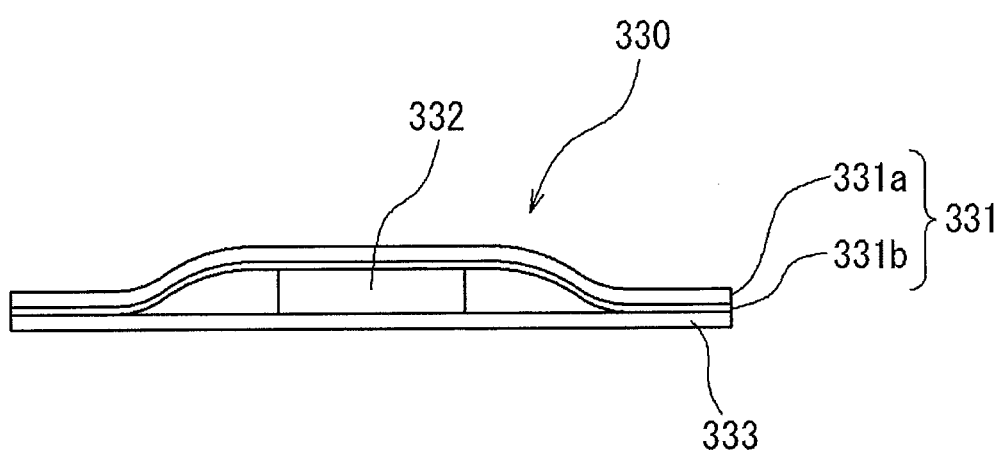
FIG. 13 is a cross-sectional view of FIG. 12 cut along A-A in FIG. 12.

FIG. 12 is a perspective view illustrating the collection member 330 including a holding sheet 331 and the collector 332 held by the holding sheet 331. FIG. 13 is a cross-sectional view of FIG. 12 cut along A-A in FIG. 12.

The collector 332 is formed of a gel having water retentivity for retaining the tissue fluid extracted from the skin of a subject, and contains an osmotic pressure adjusting agent that does not contain sodium ion. The gel is not limited in particular as long as it can collect tissue fluid. However, it is preferable that the gel is formed from at least one type of hydrophilic polymer selected from the group consisting of polyvinyl alcohol and polyvinyl pyrrolidone. The hydrophilic polymer forming the gel may be polyvinyl alcohol alone, polyvinyl pyrrolidone alone, or a mixture of them. More preferably, the gel is formed from polyvinyl alcohol alone or a mixture of polyvinyl alcohol and polyvinyl pyrrolidone.

The gel may be formed by a method of cross-linking the hydrophilic polymer in an aqueous solution. The gel may be formed by a method in which: a hydrophilic polymer aqueous solution is applied on a base material to form a coating; and the hydrophilic polymer contained in the coating is cross-linked. Examples of a method for cross-linking a hydrophilic polymer include chemical cross-linking and irradiation cross-linking. However, it is desirable to adopt irradiation cross-linking which reduce the chance of chemical substances being mixed into the gel as impurities.

In the example shown in FIG. 12 to FIG. 13, the collector 332 is in a rectangular parallelepiped shape, and the face thereof to contact with the skin has a size of 5 mm×10 mm. However, the shape and the size of the collector 332 are not limited thereto.

The holding sheet 331 includes a sheet body 331*a*, and an adhesive layer 331*b* formed on one face of the sheet body 331*a*. The face on which the adhesive layer 331*b* is formed is an adhesive face. The collector 332 is arranged substantially at the center of a release sheet 333 which also serves as a mount board. The holding sheet 331 is attached to the release sheet 333 so as to cover the collector 332. The collector 332 is held by the holding sheet 331 via part of the adhesive face of the holding sheet 331. The area of the holding sheet 331 is designed such that the holding sheet 331 is large enough to cover the collector 332 in order to prevent the collector 332 from drying at the time of collection of tissue fluid. That is, by covering the collector 332 by means of the holding sheet 331, air tightness between the skin and the holding sheet 331 can be maintained at the time of collection of tissue fluid, and thus, evaporation of moisture contained in the collector 332 can be suppressed at the time of collection of tissue fluid.

The sheet body 331*a* of the holding sheet 331 is a colorless transparent sheet or a colored transparent sheet. Accordingly, the collector 332 held by the holding sheet 331 can be readily viewed from the surface side of the sheet body 331*a* (i.e., viewed through the face that is opposite to the adhesive layer 331*b*). Preferably, the sheet body 331*a* has a low moisture permeability in order to prevent the tissue fluid from evaporating and the collector from drying. Examples of the material of the sheet body 331*a* include a polyethylene film, a polypropylene film, a polyester film, and a polyurethane film. In particular, a polyethylene film or a polyester film is preferable. The thickness of the sheet body 331*a* is not limited in particular, but is about 0.025 mm to 0.5 mm.

The collection member 330 is attached to the skin 600 of a subject by means of the adhesive face of the holding sheet 331 such that the collector 332 is placed in a micropore formation region of the subject. Then, the collector 332, placed in the micropore formation region, is left for a predetermined time period, for example, for 60 minutes or more, preferably, 120 minutes or more. Accordingly, components contained in the tissue fluid extracted through the micropores are collected in the collector 332.

[Process Procedure of Glucose Tolerance Analysis]

Next, a process procedure of analyzing the glucose tolerance of a subject using the glucose tolerance analyzing system will be described.

Figure 14:
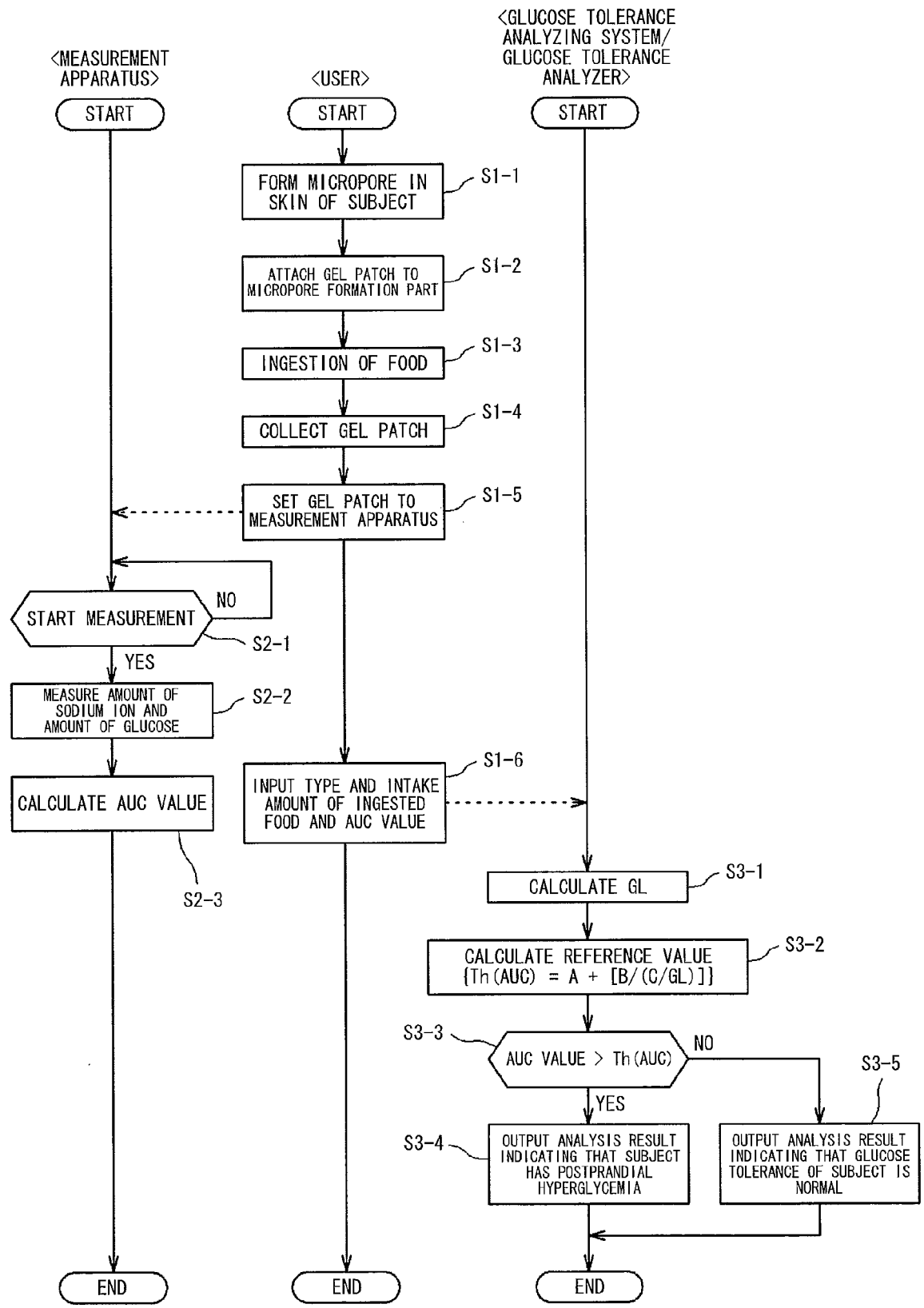
FIG. 14 is a flow chart of analysis of the glucose tolerance of a subject using a glucose tolerance analyzing system or a glucose tolerance analyzer of the present invention.

FIG. 14 is a flow chart of analysis of the glucose tolerance of a subject using the glucose tolerance analyzing system of the present invention.

First, processes by a user are performed. Here, the user is an examiner who analyzes the glucose tolerance of a subject. The user is not necessarily one person. Preferably, S1-1 to S1-4 below are performed in a health examination facility, and preferably, S1-5, S2-1 to S2-3, and S1-6 are performed in a test center that is different from the health examination facility. Further, with respect to S1-6, it is preferable that the type of food or drink and an intake amount of the food or drink are inputted in the health examination facility, and an AUC value (estimated blood glucose AUC) obtained by the measurement apparatus 300 is inputted in the test center.

In step S1-1, the user forms micropores in the skin of the subject. Specifically, the flange 375 of the micropore forming device 370, to which the microneedle chip 380 is attached, is placed such that the microneedle chip 380 can contact with the skin. Then, the user presses the release button 372 to cause the microneedles 381 of the microneedle chip 380 to contact with the skin 600 of the subject, thereby forming the micropores 601 in the skin 600.

By forming the micropores 601, extraction of tissue fluid from the skin 600 can be promoted.

In step S1-1, since the micropores 601 are formed to extract tissue fluid in this manner, burden to the subject is alleviated.

In step S1-2, the user attaches a gel patch (the collection member 330) to the part (micropore formation part) of the skin of the subject where the micropores 601 have been formed. Specifically, the user removes the micropore forming device 370 from the skin 600 of the subject. Then, the user attaches the holding sheet 331 of the collection member 330 to the skin 600 of the subject such that the collector 332 is located in the micropore formation part.

Accordingly, tissue fluid from the skin of the subject is extracted into the collection member 330, and glucose and sodium ion contained in the tissue fluid are collected and accumulated in the collector 332 of the collection member 330.

In step S1-3, the user allows the subject to ingest food or drink. In step S1-3, the type of the food or drink ingested by the subject and the intake amount of the food or drink are stored. Food or drink to be ingested by the subject is not limited in particular, as long as the corresponding GIs thereof have been determined. Such food or drink may be, for example, a prescribed meal prepared for health examination, or a meal freely selected by the subject.

In step S1-4, the user collects the gel patch (the collection member 330) attached to the skin of the subject, after two hours have elapsed since the ingestion of the food or drink was completed.

In step S1-5, the user sets the gel patch (the collection member 330) to the measurement apparatus 300. Specifically, the user attaches the gel patch (the collection member 330) to a predetermined part of the cartridge 350, and sets the cartridge 350 in the cartridge placement part 302 of the measurement apparatus 300.

Next, processes by the measurement apparatus 300 are performed.

In S2-1, the measurement apparatus accepts an instruction to start measurement of a blood glucose AUC issued from the user. When the measurement apparatus 300 has accepted the instruction to start measurement (Yes), the process is advanced to step S2-2. On the other hand, when the measurement apparatus 300 has not accepted the instruction to start measurement, step S2-1 is repeated.

In step S2-2, the measurement apparatus 300 measures the amount of sodium ion and the amount of glucose.

In step S2-3, the measurement apparatus 300 calculates an AUC value (estimated blood glucose AUC) based on the measurement values obtained in step S2-2. Specifically, the measurement apparatus 300 first calculates a glucose concentration CGlu and a sodium ion concentration CNa in the collector 332, based on the measurement values obtained in step S2-2. Subsequently, the measurement apparatus 300 calculates an estimated blood glucose AUC, based on the glucose concentration CGlu and the sodium ion concentration CNa, and based on formula (2):

$$AUC = CGlu \times V / \{\alpha \times (CNa \times V/t) + \beta\} \quad (2)$$

(wherein V represents the volume of the collector 332 of the collection member 330, t represents an extraction time period, and α and β represent constants determined by experiments.) The principle for calculating an estimated blood glucose AUC based on formula (2) is described in detail in International Publication WO2010/013808.

Next, processes by the user are performed.

In step S1-6, the user inputs the type of food or drink ingested by the subject and the intake amount of the food or drink, and the AUC value obtained by the measurement apparatus 300 (estimated blood glucose AUC), to the terminal 100 of the glucose tolerance analyzing system 1.

As shown in FIG. 15, the input screen of the terminal 100 includes an item A1 for inputting the type of the ingested food or drink and an item A2 for inputting the intake amount of the food or drink, which are meal information, and an item A3 for inputting the AUC value (estimated blood glucose AUC). A pull-down system is adopted for the item A1. Accordingly, the user can easily input the type of the food or drink ingested by the subject. The terminal 100 transmits the inputted information to the server 200.

Then, processes by the glucose tolerance analyzing system 1 are performed. Processes of S3-1 to S3-5 are realized by the reference value calculation/comparison determination program stored in the hard disk 223 of the server 200.

In step S3-1, the CPU 220 of the server 200 calculates a GL value based on the inputted type of the food or drink ingested by the subject and the inputted intake amount of the food or drink.

Here, the GL value is a numerical value that is based on a value obtained by multiplying a glycemic index (GI) by the weight of carbohydrate, and is an index representing the degree of increasing the blood glucose level. The GL value can be calculated based on formula (3):

$$GL\ value = [GI1 \times D1 + GI2 \times D2 + \ldots + GIn \times Dn]/100 \quad (3)$$

(wherein GIn represents the GI of the food or drink and Dn represents the intake amount of the food or drink.)

It should be noted that the GI of food or drink is a value publicly available, for example, in a web page, http://fmx01dhs.ucc.usyd.edu.au/Sugirs/index.php.

In step S3-2, the CPU 220 calculates a reference value for analyzing the glucose tolerance of the subject, based on the GL value obtained in step S3-1, in accordance with a predetermined calculation formula.

An example of the above calculation formula is formula (1):

$$\text{reference value}(Th(AUC)) = A + [B/(C/GL)] \quad (1)$$

(wherein, A represents a fasting-blood-glucose-based two-hour blood glucose AUC value, B represents a reference value corresponding to an increase in the blood glucose level, C represents a glycemic load corresponding to a given amount of glucose (e.g., 75 g) (thus, glycemic load is 75), and GL represents a glycemic load (i.e., the GL value obtained in step S3-1) calculated based on a glycemic index corresponding to the food or drink ingested by the subject and based on the intake amount of the food or drink.)

Here, the fasting-blood-glucose-based two-hour blood glucose AUC value is a value determined in advance by multiplying 2 by the fasting blood glucose level of the subject. As the fasting blood glucose level of the subject, for example, 90 mg/dL being a standard value for fasting blood glucose levels may be used, or a value measured through blood collection at the time of health examination may be used. When 90 mg/dL is used as the fasting blood glucose level, the two-hour blood glucose AUC value is 180 mg·h/dL.

The above-described reference value corresponding to an increase in the blood glucose level is a value obtained by subtracting the fasting-blood-glucose-based two-hour blood glucose AUC value from a reference value (Th(AUC)) for a 75 g oral glucose tolerance test (OGTT). For example, in the case where the reference value (Th(AUC)) for a 75 g OGTT is 300 mg·h/dL, and the fasting-blood-glucose-based two-hour blood glucose AUC value is 180 mg·h/dL, the reference value corresponding to an increase in the blood glucose level is 120 (i.e., 300-180) mg·h/dL.

It should be noted that, in the present embodiment, the reference value (Th(AUC)) is calculated by using formula (1), based on information obtained from a 75 g OGTT and a diabetes diagnostic criteria of Japan Diabetes Society (a reference value (300 mg/dL) for a 75 g OGTT and a standard value (90 mg/dL) for fasting blood glucose levels). However, the present invention is not limited to the embodiment. That is, information obtained from a 75 g OGTT (B and C in formula (1)) can be changed as appropriate, in accordance with the amount of glucose used in the oral glucose tolerance test.

By using formula (1) and the blood glucose AUC (estimated blood glucose AUC in this case), the type of the glucose tolerance of the subject can be discriminated. Accordingly, it is possible to alleviate burden to the patient at the time of glucose tolerance analysis, and to perform the glucose tolerance analysis simply and with a high accuracy.

In step S3-3, the CPU 220 analyzes the glucose tolerance of the subject based on the reference value obtained in step S3-2 and the AUC value (estimated blood glucose AUC in this case) inputted in step S1-6. Specifically, the glucose tolerance analyzing system 1 analyzes the glucose tolerance of the subject based on whether the AUC value is greater than the reference value.

When AUC value>Th(AUC) is satisfied, the process is advanced to step S3-4, and the CPU 220 generates an analysis result indicating that the subject has abnormal glucose tolerance (postprandial hyperglycemia). The generated information is transmitted to the terminal 100.

Figure 16:
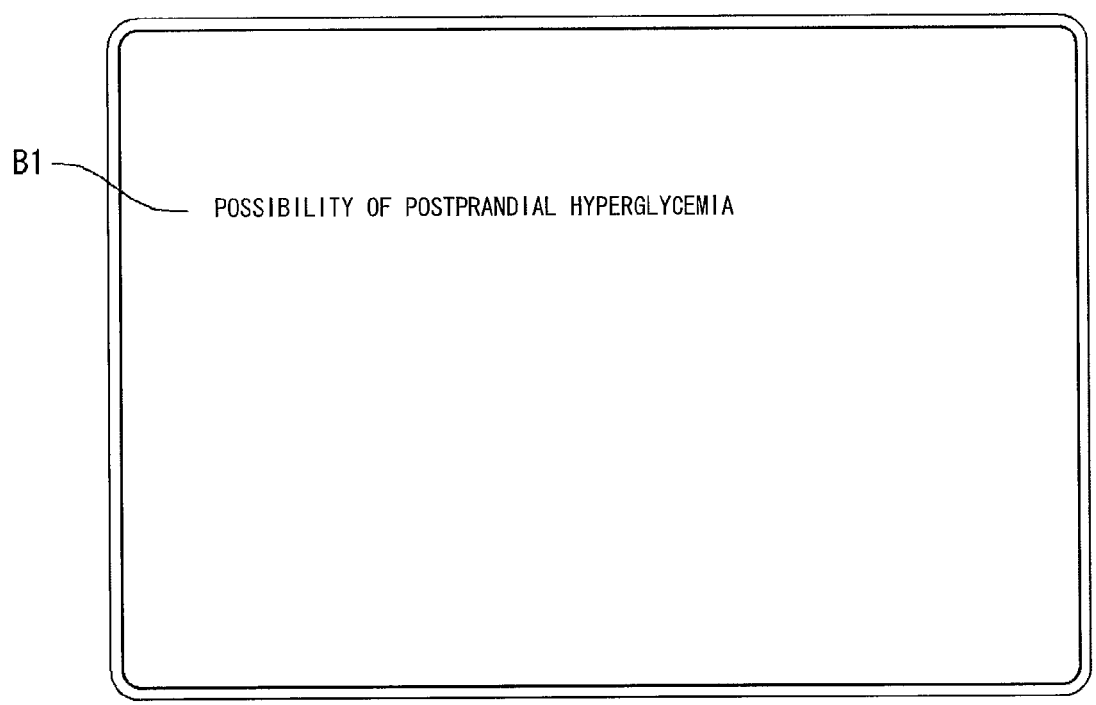
FIG. 16 shows one example of an output screen.

The display 100a of the terminal 100 displays the received analysis result. At this time, for example, an analysis result B1 "possibility of postprandial hyperglycemia" is displayed on the output screen as shown in FIG. 16. It should be noted that the analysis result displayed on the output screen is not limited to the above, and an analysis result such as "possibility of abnormal glucose tolerance or diabetic type" may be displayed, for example.

On the other hand, when AUC value>Th(AUC) is not satisfied, the process is advanced to step S3-5, and the CPU 220 generates an analysis result indicating that the glucose tolerance of the subject is normal, and transmits the analysis result to the terminal 100. The display 100a of the terminal 100 displays the received analysis result. At this time, for example, an analysis result "normal type" is displayed on the output screen.

Since the information regarding the type of the ingested food or drink and the information regarding the intake amount have been inputted to the glucose tolerance analyzing system 1 by user in step S1-6, the glucose tolerance analyzing system 1 may cause the display 100a to output information regarding nutrition guidance based on the ingested meal. For example, in the case where the content of the meal ingested by the subject is a combination of carbohydrates (e.g., combination of udon (Japanese wheat noodles) and inari-zushi (flavored boiled rice wrapped up with fried bean curd), combination of okonomiyaki (Japanese savory pancake containing a variety of ingredients) and rice, and combination of Chinese noodles and fried rice), the reference value based on the type of the ingested food or drink is 290, and the blood glucose AUC of the subject is 320, it can be inferred that the habit of selecting such a meal content may be a cause of abnormal glucose tolerance such as postprandial hyperglycemia. Therefore, in this case, as information regarding nutrition guidance, it is possible to output specific guidance information for improving glucose tolerance, such as: "examples of good combination of food or drink", "the order of eating food or drink (e.g., eat vegetables first)", "alternatives of the combination of the ingested food or drink". Preferably, information regarding nutrition guidance is stored in advance in the hard disk 123, 223, or the like, in accordance with, for example, patterns of meal contents and the like.

As described above, according to the glucose tolerance analyzing system 1 of the present embodiment, even when a subject has taken any type of meal, it is possible to analyze the glucose tolerance of the subject by inputting, to the glucose tolerance analyzing system 1, information regarding the type of the food or drink ingested by the subject, information regarding the intake amount of the food or drink, and information regarding the amount of glucose in the subject after the ingestion of the food or drink. Therefore, unlike conventional technologies, an oral glucose tolerance test need not to be performed, and thus burden to the subject can be alleviated.

It should be noted that, in the above embodiment, the AUC value (estimated blood glucose AUC in this case) is determined based on the amount of sodium ion and the amount of glucose contained in the tissue fluid. However, the present invention is not limited to the embodiment. For example, self-monitoring of blood glucose (SMBG) is performed at forearm capillaries at intervals of 15 minutes when the blood glucose level is fluctuating, or at intervals of 30 minutes or more when the blood glucose level is stable, whereby an AUC value (blood glucose AUC in this case) may be determined by a trapezoidal approximation method by using the obtained SMBG value.

Further, in the above embodiment, GI is used as an index regarding blood glucose increase due to food or drink. However, the present invention is not limited to the embodiment. For example, the amount of carbohydrate, the degree of calorie increase for each type of food or drink, or the like may be used as the index regarding blood glucose increase due to food or drink.

[Verification of Effects]

Effects of using a reference value calculated in accordance with formula (1) in analysis of the glucose tolerance of a subject will be verified.

After a series of tests such as physical measurement and blood collection in a health examination, an inner forearm of each of 50 subjects was sterilized with ethanol-soaked cotton, and micropores were formed, at a puncture speed of 6 m/s, on the skin of each subject by using the micropore forming device 370 to which the microneedle chip 380 (microneedle length=300 µm, the number of microneedles=305) shown in FIG. 9 had been attached.

It should be noted that subjects were classified in advance as follows in accordance with the types of glucose tolerance.

1: normal type

2: impaired fasting glycemia (the blood glucose level is higher than a reference value only during fasting, but blood glucose increase after a meal is classified as normal type)

3: abnormal glucose tolerance A (the blood glucose level after two hours have elapsed since a meal exceeds a reference value, but the blood glucose level after one hour has elapsed since a meal is lower than a reference value)

4: abnormal glucose tolerance B (the blood glucose level after one hour has elapsed since a meal is higher than the reference value)

5: diabetic type

Next, the collection member 330 was attached to the micropore formation part (extraction area: 5 mm×10 mm) on the skin of each subject. Then, the subject was allowed to ingest a prescribed diet (brand name: JANEF E460F18 produced by Kewpie Corporation). The GL value of the prescribed diet is about 50. After two hours elapsed since the ingestion of the prescribed diet was completed, the collection member 330 was collected and only the hydrogel (collector) was removed from the collection member 330. The obtained hydrogel (collector) was immersed in 5 mL purified water to be left overnight in a refrigerator whose inside temperature was set to 4° C., whereby living body components accumulated in the hydrogel was collected.

The amount of glucose and the amount of sodium ion in the tissue fluid extracted in the collected collection member 330 were measured. The amount of glucose was measured by the GOD fluorescence absorbance method. The amount of sodium ion was measured by an ion chromatograph.

Next, a glucose concentration CGlu and a sodium ion concentration CNa in the collector 332 of the collection member 330 were calculated based on the amount of glucose and the amount of sodium ion. Subsequently, an estimated two-hour postprandial blood glucose AUC value was calculated based on the glucose concentration CGlu and the sodium ion concentration CNa, and based on formula (2). The volume of the collector 332 was 5 mm×10 mm×0.3 mm.

Next, a reference value was calculated in accordance with formula (1) as shown below. As a fasting-blood-glucose-based two-hour blood glucose AUC value, a value (160) was used which was obtained by multiplying 2 by the value measured through blood collection at the health examination. Thus, in formula (1), "A" was 160 and "B" was 140 (i.e., 300-160=140).

$$\text{Reference value } (Th(AUC)) = A + [B/(C/GL)]$$
$$= 160 + [140/(75/50)]$$
$$= 253$$

Figure 17B:
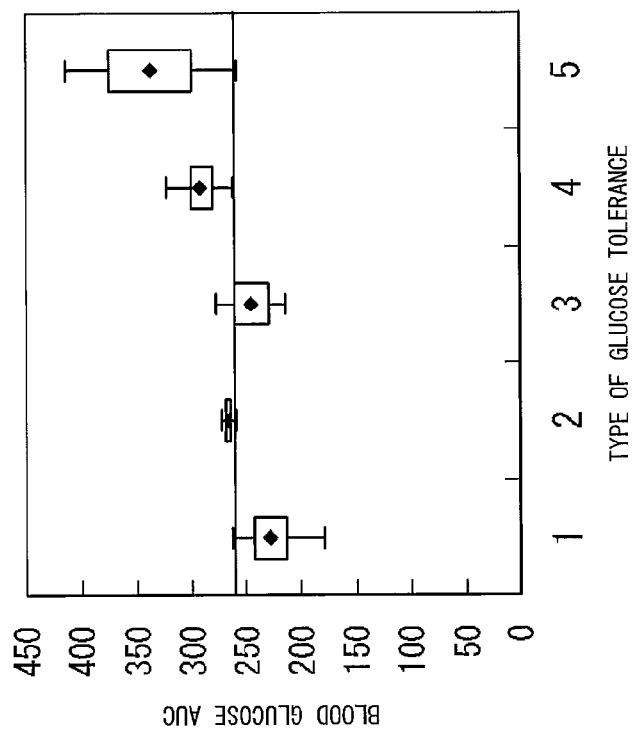
FIG. 17B is a graph showing a result of study of the relationship between the type of glucose tolerance and the blood glucose AUC.
Figure 17A:
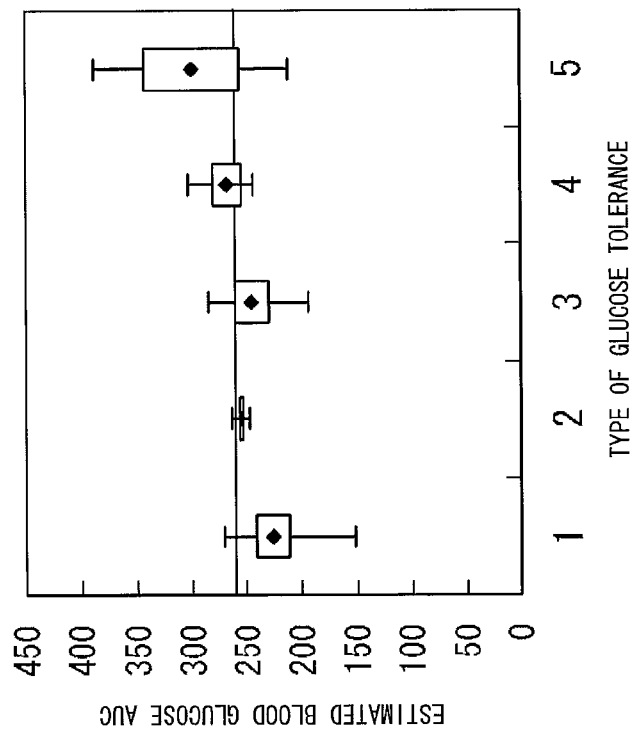
FIG. 17A is a graph showing a result of study of the relationship between the type of glucose tolerance and the estimated blood glucose AUC.

The result of the study of the relationship between the type of glucose tolerance and the estimated blood glucose AUC is shown in FIG. 17A.

Further, with respect to the postprandial blood glucose of each subject, self-monitoring of blood glucose (SMBG) using fingertip capillary blood was performed at intervals of one hour, and a blood glucose AUC was calculated by the trapezoidal approximation method, based on the obtained blood glucose levels and the fasting blood glucose level obtained at the health examination. The result of the study of the relationship between the type of glucose tolerance and the blood glucose AUC is shown in FIG. 17B. In FIGS. 17A and 17B, numerals 1 to 5 correspond to the types 1 to 5 of glucose tolerance of subjects above.

From the results shown in FIGS. 17A and 17B, it is understood that the abnormal glucose tolerance B and the diabetic type are clearly discriminated from the other types of glucose tolerance, by the reference value calculated in accordance with formula (1). Accordingly, it is understood that the reference value calculated in accordance with formula (1) is useful for analyzing the glucose tolerance of a subject.

[Modification]

The above embodiment has described an example in which glucose tolerance is analyzed based on whether the blood glucose AUC (or estimated blood glucose AUC) exceeds the reference value. However, the present invention is not limited to the embodiment. For example, a predetermined range (hereinafter referred to as "gray area") is set based on the reference value, and the glucose tolerance may be analyzed based on the gray area. In this case, the following criteria and analysis results may be provided.

1) when the blood glucose AUC (or estimated blood glucose AUC) exceeds the gray area
    . . . diabetic type
2) when the blood glucose AUC (or estimated blood glucose AUC) is within the gray area
    . . . either impaired fasting glycemia or abnormal glucose tolerance
3) when the blood glucose AUC (or estimated blood glucose AUC) is below the gray area
    . . . normal type.

Embodiment 2

The present embodiment is a glucose tolerance analyzer implemented by a computer that includes: an accepting section which accepts inputs of information regarding the type of food or drink ingested by a subject, information regarding the intake amount of the food or drink, and information regarding the amount of glucose in the subject after the ingestion of the food or drink; an output section which outputs an analysis result; a storage section which stores indices regarding blood glucose increase due to food or drink and a calculation formula for calculating a reference value for analyzing the glucose tolerance of the subject; and a controller which calculates a reference value for analyzing the glucose tolerance of the subject, analyzes the glucose tolerance of the subject, and outputs an obtained analysis result.

Figure 18:
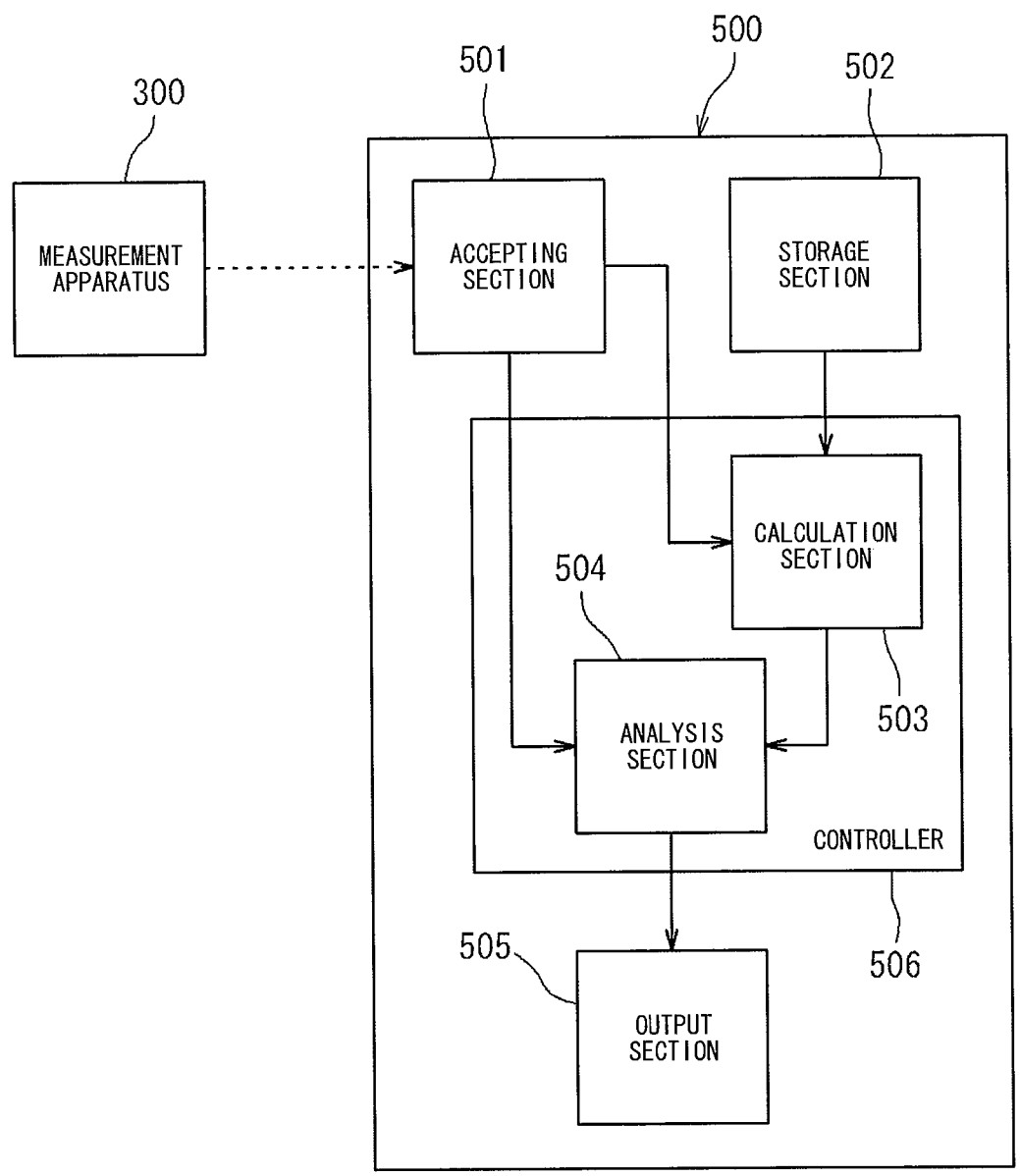
FIG. 18 is a block diagram showing a functional configuration of a glucose tolerance analyzer according to one embodiment of the present invention.

FIG. 18 is a block diagram showing a functional configuration of a glucose tolerance analyzer according to one embodiment of the present invention. This glucose tolerance analyzer is an apparatus in which the terminal 100 and the server 200 in embodiment 1 are integrally formed.

As shown in FIG. 18, a glucose tolerance analyzer 500 is a computer that includes an accepting section 501, a storage section 502, a calculation section 503, an analysis section 504, and an output section 505. In the present embodiment, the calculation section 503 and the analysis section 504 constitute a controller 506.

The accepting section 501 accepts inputs of information regarding the type of food or drink ingested by a subject, information regarding the intake amount of the food or drink, and information regarding the amount of glucose in the subject after the ingestion of the food or drink. The storage section 502 stores indices regarding blood glucose increase due to food or drink, and a calculation formula for calculating a reference value for analyzing the glucose tolerance of the subject. The calculation section 503 calculates a reference value for analyzing the glucose tolerance of the subject based on the information regarding the type of the food or drink ingested by the subject, the information regarding the intake amount of the food or drink, which were accepted by the accepting section 501, and based on the indices stored in the storage section 502, in accordance with the calculation formula stored in the storage section 502. The analysis section 504 analyzes the glucose tolerance of the subject based on the information regarding the amount of glucose accepted by the accepting section 501 and based on the reference value calculated by the calculation section 503. The output section outputs an analysis result obtained by the analysis section 504.

The flow chart of the process procedure of analyzing the glucose tolerance of a subject using the glucose tolerance analyzer 500 according to the present embodiment is similar to the flow chart of the process procedure of analyzing the glucose tolerance of a subject using the glucose tolerance analyzing system 1 described above.

As described above, according to the glucose tolerance analyzer 500 of the present embodiment, even when a subject has taken any type of meal, it is possible to analyze the glucose tolerance of the subject by inputting, to the glucose tolerance analyzer 500, information regarding the type of the consumables ingested by the subject, information regarding the intake amount of the consumables, and information regarding the amount of glucose in the subject after the ingestion of the food or drink. Therefore, according to the glucose tolerance analyzer 500 of the present embodiment, an oral glucose tolerance test as in conventional technologies need not to be performed, similarly to the case of the glucose tolerance analyzing system 1 described above, and thus, burden to the subject can be alleviated.

<Other Modifications>

In the glucose tolerance analyzing system 1 and the glucose tolerance analyzer 500, the accepting sections 101 and 501 may be communicably connected to the measurement apparatus 300. In this case, the information regarding the amount of glucose after the ingestion of the food or drink which is obtained by the measurement apparatus 300 can be directly transmitted to the accepting sections 101 and 501. This eliminates the necessity of the user inputting the information regarding the amount of glucose after ingestion of food or drink.

What is claimed is:

1. A glucose tolerance analyzer comprising:
an accepting section configured to accept inputs of information regarding a type of food or drink ingested by a subject, information regarding an intake amount of the food or drink, and information regarding an amount of glucose in tissue fluid accumulated in a collector comprising a laminated structure and configured to contact a skin of the subject after the ingestion of the food or drink;
an output section configured to output an analysis result of glucose tolerance; and
a controller configured to:
calculate a reference value for analyzing glucose tolerance of the subject based on the accepted information regarding the type of the food or drink ingested by the subject and the information regarding the intake amount of the food or drink, and based on a predetermined index regarding blood glucose increase due to food or drink,
wherein the reference value is expressed as $(Th(AUC)) = A + (B/(C/GL))$,
where A represents a fasting-blood-glucose-AUC value, B represents a reference value corresponding to an increase in a blood glucose level, C represents a glycemic load corresponding to a given amount of glucose, and GL represents a glycemic load calculated based on a glycemic index corresponding to the food or drink ingested by the subject and the intake amount of the food or drink;
analyze the glucose tolerance of the subject based on the accepted information regarding the amount of glucose and based on the calculated reference value, such that a type of glucose tolerance is discriminated; and
control the output section to output an obtained analysis result as an analysis result of glucose tolerance.

2. The glucose tolerance analyzer of claim 1, wherein the index regarding blood glucose increase due to food or drink comprises a glycemic index.

3. The glucose tolerance analyzer of claim 1, wherein the accepted information regarding the amount of glucose comprises an area under blood glucose concentration-time curve (blood glucose AUC) or a value corresponding to the blood glucose AUC.

4. The glucose tolerance analyzer of claim 3, wherein A represents a fasting-blood-glucose-based two-hour blood glucose AUC value.

5. The glucose tolerance analyzer of claim 1, wherein the accepted information regarding the amount of glucose is information regarding the amount of glucose in the tissue fluid accumulated in the collector, after the ingestion of the food or drink, from skin of the subject on which a process for promoting extraction of the tissue fluid from the skin has been performed.

6. The glucose tolerance analyzer of claim 5, wherein the amount of glucose comprises an amount of glucose in the tissue fluid collected in the collector, after two hours have elapsed since the ingestion of the food or drink, or after two hours have elapsed with the collector being in contact with the skin.

7. The glucose tolerance analyzer of claim 5, wherein the accepted information regarding the amount of glucose comprises a numerical value obtained by correcting the amount of glucose in the tissue fluid by an amount of an inorganic ion in the tissue fluid.

8. The glucose tolerance analyzer of claim 7, wherein the inorganic ion comprises a sodium ion.

9. The glucose tolerance analyzer of claim 1, wherein when the accepted information regarding the amount of glucose is information indicating that the amount of glucose exceeds the reference value, the controller generates an analysis result indicating that the subject has abnormal glucose tolerance.

10. The glucose tolerance analyzer of claim 1, wherein when the accepted information regarding the amount of glucose is information indicating that the amount of glucose is less than or equal to the reference value, the controller generates an analysis result indicating that the subject does not have abnormal glucose tolerance.

11. The glucose tolerance analyzer of claim 1, further comprising:
an obtaining section configured to obtain information regarding nutrition guidance based on the accepted information regarding the type of the food or drink ingested by the subject and based on the analysis result generated by the controller,
wherein the controller further controls the output section to output the information obtained by the obtaining section.

12. A glucose tolerance analyzing system comprising:
a collector comprising a laminated structure in contact with the skin of a subject and configured to accumulate tissue fluid from the subject;
a first information processing apparatus and a second information processing apparatus, wherein
the first information processing apparatus comprises:
an accepting section configured to accept inputs of information regarding a type of food or drink ingested by the subject, information regarding an intake amount of the food or drink, and information regarding an amount of glucose in the tissue fluid of the subject after the ingestion of the food or drink;
a first transmission section configured to transmit the information accepted by the accepting section, to the second information processing apparatus;
a first reception section configured to receive an analysis result of glucose tolerance of the subject from the second information processing apparatus; and
an output section configured to output the analysis result received by the first reception section, and
the second information processing apparatus comprises:
a second reception section configured to receive the information transmitted from the first transmission section;
a controller configured to calculate a reference value for analyzing the glucose tolerance of the subject based on the received information regarding the type of the food or drink ingested by the subject and the received information regarding the intake amount of the food or drink, and based on a predetermined index regarding blood glucose increase due to food or drink,
wherein the reference value is expressed as $(Th(AUC)) = A + (B/(C/GL))$,
where A represents a fasting-blood-glucose-based AUC value, B represents a reference value corresponding to an increase in a blood glucose level, C represents a glycemic load corresponding to a given amount of glucose, and GL represents a glycemic load calculated based on a glycemic index corresponding to the food or drink ingested by the subject and the intake amount of the food or drink, and the controller is further configured to analyze the glucose tolerance of the subject based on the received information regarding the amount of glucose in the tissue fluid of the subject received by the second reception section and based on the calculated reference value, such that a type of glucose tolerance is discriminated;

and a second transmission section configured to transmit an analysis result obtained by the controller to the first information processing apparatus.

13. The glucose tolerance analyzing system of claim 12, wherein the index regarding blood glucose increase due to food or drink comprises a glycemic index.

14. The glucose tolerance analyzing system of claim 12, wherein the received information regarding the amount of glucose is an area under blood glucose concentration-time curve (blood glucose AUC) or a value corresponding to the blood glucose AUC.

15. The glucose tolerance analyzing system of claim 14, wherein A represents a fasting-blood-glucose-based two-hour blood glucose AUC value.

16. The glucose tolerance analyzing system of claim 12, wherein the received information regarding the amount of glucose is information regarding an amount of glucose in the tissue fluid collected, after the ingestion of the food or drink, from the skin of the subject on which a process for promoting extraction of the tissue fluid from the skin has been performed.

17. A glucose tolerance analyzing method comprising:
providing a collector comprising a laminated structure in contact with the skin of a subject and configured to accumulate tissue fluid from the subject;
an accepting step of accepting inputs of information regarding a type of food or drink ingested by a subject, information regarding an intake amount of the food or drink, and information regarding an amount of glucose in the tissue fluid of the subject after the ingestion of the food or drink;
an output step of outputting an analysis result of glucose tolerance; and
a control step of:
calculating a reference value for analyzing glucose tolerance of the subject based on the accepted information regarding the type of the food or drink ingested by the subject and the accepted information regarding the intake amount of the food or drink, and based on a predetermined index regarding blood glucose increase due to food or drink
wherein the reference value is expressed as (Th (AUC))=A+(B/(C/GL)),
where A represents a fasting-blood-glucose-based AUC value, B represents a reference value corresponding to an increase in a blood glucose level, C represents a glycemic load corresponding to a given amount of glucose, and GL represents a glycemic load calculated based on a glycemic index corresponding to the food or drink ingested by the subject and the intake amount of the food or drink;
analyzing the glucose tolerance of the subject based on the accepted information regarding the amount of glucose and based on the calculated reference value, such that a type of glucose tolerance is discriminated; and
controlling an obtained analysis result to be outputted in the output step as an analysis result of glucose tolerance.

18. The glucose tolerance analyzing method of claim 17, wherein the index regarding blood glucose increase due to food or drink comprises a glycemic index.

19. A non-transitory storage medium having stored thereon computer-executable programs executed by at least one processor of a computer system which is connected to an output device and an input device, the programs controlling the at least one processor to perform the steps of:
controlling an accepting section to accept, via the input device, inputs of information regarding a type of food or drink ingested by a subject, information regarding an intake amount of the food or drink, and information regarding an amount of glucose in the subject after the ingestion of the food or drink;
calculating a reference value for analyzing glucose tolerance of the subject based on the accepted information regarding the type of the food or drink ingested by the subject and the accepted information regarding the intake amount of the food or drink, and based on a predetermined index regarding blood glucose increase due to food or drink,
wherein the reference value is expressed as (Th (AUC))=A+(B/(C/GL)),
where A represents a fasting-blood-glucose-based blood glucose AUC value, B represents a reference value corresponding to an increase in a blood glucose level, C represents a glycemic load corresponding to a given amount of glucose, and GL represents a glycemic load calculated based on a glycemic index corresponding to the food or drink ingested by the subject and the intake amount of the food or drink;
analyzing the glucose tolerance of the subject based on the accepted information regarding the amount of glucose accepted by the accepting section and based on the calculated reference value, such that a type of glucose tolerance is discriminated; and
controlling the output device to output an obtained analysis result.

* * * * *